(12) United States Patent  
Dertinger

(10) Patent No.: US 8,187,826 B2  
(45) Date of Patent: **\*May 29, 2012**

(54) QUANTITATIVE ANALYSIS OF IN VIVO MUTATION AT THE PIG-A LOCUS

(75) Inventor: Stephen D. Dertinger, Webster, NY (US)

(73) Assignee: Litron Laboratories, Ltd., Rochester, NY (US)

( \* ) Notice: Subject to any disclaimer, the term of this patent is extended or adjusted under 35 U.S.C. 154(b) by 329 days.

This patent is subject to a terminal disclaimer.

(21) Appl. No.: 12/483,829

(22) Filed: Jun. 12, 2009

(65) Prior Publication Data

US 2009/0311706 A1 Dec. 17, 2009

Related U.S. Application Data

(60) Provisional application No. 61/061,031, filed on Jun. 12, 2008.

(51) Int. Cl.
- *G01N 33/00* (2006.01)
- *G01N 1/00* (2006.01)
- *G01N 21/64* (2006.01)
- *A61K 49/00* (2006.01)

(52) U.S. Cl. .................. 435/7.25; 435/7.21; 435/287.2; 435/334; 435/355; 435/973; 436/521; 436/522; 436/10; 436/17; 436/63; 436/94; 436/172; 436/175; 436/811; 422/73; 422/82.08; 424/9.2

(58) Field of Classification Search ................ 435/7.21, 435/7.23, 7.24, 7.25, 287.2, 334, 355, 973; 436/521, 522, 536, 548, 10, 17, 63, 64, 94, 436/172, 175, 177, 811; 422/73, 82.05, 82.08; 424/7.2, 9.2

See application file for complete search history.

(56) References Cited

U.S. PATENT DOCUMENTS

| | | | |
|---|---|---|---|
| 5,314,805 A | 5/1994 | Haugland et al. | |
| 5,858,667 A | 1/1999 | Dertinger et al. | |
| 5,859,667 A | 1/1999 | Kondo et al. | |
| 6,100,038 A \* | 8/2000 | Dertinger et al. ............ | 435/6.13 |
| 6,593,095 B1 | 7/2003 | Buckley et al. | |
| 7,358,059 B2 \* | 4/2008 | Orfao De Matos Correia E Vale ............................. | 435/7.21 |
| 7,824,874 B2 \* | 11/2010 | Dertinger ..................... | 435/7.25 |
| 2003/0138851 A1 | 7/2003 | De Matos et al. | |
| 2005/0042602 A1 | 2/2005 | Ahearn et al. | |
| 2006/0040291 A1 | 2/2006 | Dertinger et al. | |
| 2006/0140963 A1 | 6/2006 | Young et al. | |
| 2007/0274919 A1 | 11/2007 | Dertinger | |

OTHER PUBLICATIONS

Albertini, "Somatic Mutation Models of Relevance for Humans," Environmental Mutagen Society, Meeting Abstracts, No. 8 (p. 161) (May 2003).

Chen et al., "Glycophosphatidylinositol-anchored Protein Deficiency as a Marker of Mutator Phenotypes in Cancer," Cancer Research 61:654-8 (2001).

Wang et al., "Clinical Significance of a Minor Population of Paroxysmal Nocturnal Hemoglobinuria-type Cells in Bone Marrow Failure Syndrome," Blood 100(12):3897-902 (2002).

(Continued)

*Primary Examiner* — Gail R Gabel

(74) *Attorney, Agent, or Firm* — LeClairRyan, a Professional Corporation

(57) ABSTRACT

The invention relates to methods and kits for the quantitative analysis of in vivo mutation frequencies of the Pig-A gene in individuals exposed to a genotoxicant, particularly using peripheral blood samples of vertebrates.

22 Claims, 12 Drawing Sheets

OTHER PUBLICATIONS

Ware et al., "Immunophenotypic Analysis of Reticulocytes in Paroxysmal Nocturnal Hemoglobinuria," Blood 86 (4):1586-9 (1995).

Araten et al., "A Quantitative Measurement of the Human Somatic Mutation Rate," Cancer Res 65(18):8111-8117 (2005).

Russell E. Ware, "Is There a Little PNH in All of Us?," Blood 105(10):3760-3761 (2005).

Hernandez-Campo et al., "Comparative Analysis of Different Flow Cytometry-Based Immunophenotypic Methods for the Analysis of CD59 and CD55 Expression on Major Peripheral Blood cell Subsets," Cytometry (Clinical Cytometry) 50:191-201 (2002).

Parker et al., "Diagnosis and Management of Paroxysmal Nocturnal Hemoglobinuria," Blood 106(12):3699-3709 (2005).

Bryce et al., "In vivo Mutation Assay Based on the Endogenous Pig-a Locus," Environ Mol Mutagen 49(4):256-264 (2008).

Hernandez-Campo et al., "Quantitative Analysis of the Expression of Glycosylphosphatidylinositol-Anchored Proteins During the Maturation of Different Hematopoietic Cell Compartments of Normal Bone Marrow," Cytometry Part B (Clinical Cytometry) 72B:34-42 (2007).

Miura et al., "Development of an In Vivo Gene Mutation Assay Using the Endogenous Pig-A Gene: I. Flow Cytometric Detection of CD59-Negative Peripheral Red Blood Cells and CD48-Negative Spleen T-Cells from the Rat," Environ Mol Mutagen 49:614-621 (2008).

Miura et al., "Development of an In vivo Gene Mutation Assay Using the Endogenous Pig-A Gene: I. Flow Cytometric Detection of CD-59-Negative Peripheral Red Blood Cells and CD48-Negative Spleen T-Cells from the Rat," Environmental and Molecular Mutagenesis 49:614-621 (2008).

International Search Report for International Patent Application No. PCT/US09/47201 (Jul. 31, 2009).

Written Opinion of the International Searching Authority for International Patent Application No. PCT/US09/47201 (Jul. 23, 2009).

* cited by examiner

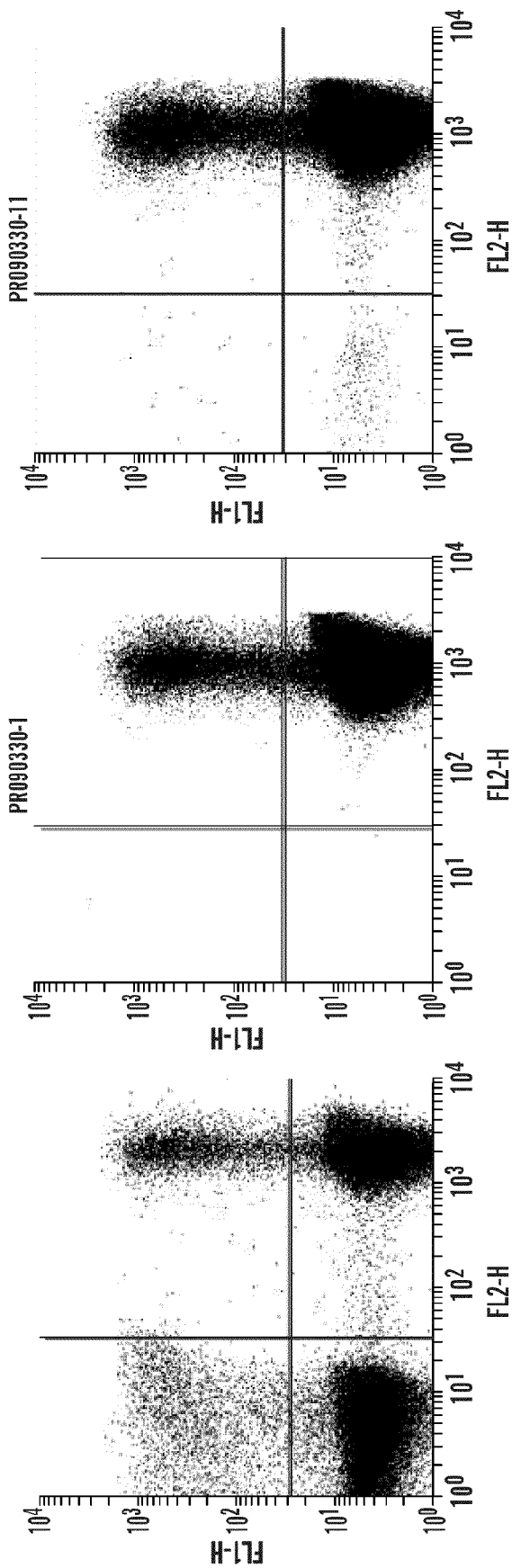

QUANTITATIVE ANALYSIS OF IN VIVO MUTATION AT THE *PIG-A* LOCUS

The present application claims the priority benefit of U.S. Provisional Patent Application Ser. No. 61/061,031, filed Jun. 12, 2008, which is hereby incorporated by reference in its entirety.

FIELD OF THE INVENTION

The present invention relates to methods and materials for the quantitative analysis of in vivo mutation rates in individuals exposed to a genotoxicant, particularly using peripheral blood samples of vertebrates.

BACKGROUND OF THE INVENTION

Several authors have articulated the possibility of using the endogenous Pig-A gene as a reporter of somatic mutation (Araten et al, "Clonal Populations of Hematopoietic Cells with Paroxysmal Nocturnal Hemoglobinuria Genotype and Phenotype are Present in Normal Individuals," *Proc Natl Acad Sci USA* 96:5209-5214 (1999); Chen et al., "Glycophosphatidylinositol-anchored Protein Deficiency as a Marker of Mutator Phenotypes in Cancer," *Cancer Res.* 61:654-658 (2001)). As with the HPRT locus, Pig-A is located on the X-chromosome. Iida and colleagues isolated the human genomic gene, and found that it contains six exons over its 17 kb length (Iida et al., "Characterization of Genomic PIG-A Gene: A Gene for GPI Anchor Biosynthesis and Paroxysmal Nocturnal Hemoglobinuria," *Blood* 83:3126-3131 (1994)). As demonstrated by Kawagoe et al., "Molecular cloning of Murine pig-a, a Gene for GPI-anchor Biosynthesis, and Demonstration of Interspecies Conservation of its Structure, Function, and Genetic Locus," *Genomics* 23:566-574 (1994), there is a high degree of interspecies conservation of the gene's structure, function, and locus. The Pig-A gene product acts in the first step in glycosylphosphatidylinositol (GPI) anchor biosynthesis, and the entire process is thought to require at least 12 genes. Mutation of any one of these could theoretically result in GPI anchor deficiency. However, all other genes involved in GPI anchor synthesis are autosomal. Mutations on both alleles would have to occur to ablate expression of GPI anchors, and this is expected to be a very rare event. Thus, an inability to anchor GPI-linked proteins in the outer membrane is believed to be virtually equivalent to Pig-A mutation.

This key assumption, as well as practical aspects of assay development, greatly benefit from research on Paroxysmal Nocturnal Hemoglobinuria (PNH). PNH is a genetic disorder that affects 1 to 10 per million individuals, and is caused by a somatic Pig-A gene mutation within a bone marrow stem cell (Norris et al., "The Defect in Glycosylphosphatidylinositol Anchor Synthesis in Paroxysmal Nocturnal Hemoglobinuria," *Blood* 83:816-821 (1994)). Since bone marrow stem cells are the precursors for the entire hematopoietic system, the gene mutation tends to affect numerous lineages. Erythrocytes, granulocytes and monocytes are typically affected. In a minority of cases, however, lymphocytes are also affected. A key finding is that all PNH clones to date exhibit mutation at the Pig-A locus (Nishimura et al., "Paroxysmal Nocturnal Hemoglobinuria: An Acquired Genetic Disease," *Am J Hematol* 62:175-182 (1999)). Furthermore, an analysis of 146 PNH patients by Nishimura and colleagues provides important examples of the types of mutations that lead to GPI anchor deficiency. Single-base substitutions and frame-shift events are the most highly represented classes of mutation observed. Even so, there are three examples of large deletions (entire gene, 4 kb, and 737 base pairs), as well as a large insertion (88 base pairs). The mutations are widely distributed in the coding regions and splice sites, although others have found a somewhat higher frequency of missense mutations in exon 2 relative to other exons (Nafa et al., "The Spectrum of Somatic Mutations in the PIG-A Gene in Paroxysmal Nocturnal Hemoglobinuria Includes Large Deletions and Small Duplications," *Blood Cells Mol Dis* 24:370-384 (1998)). Taken together, the PNH literature provides strong evidence that an in vivo assay based on the Pig-A gene would be sensitive to each important class of mutation.

In a report by Miura et al., "Development of an In Vivo Gene Mutation Assay Using the Endogenous Pig-A Gene: I. Flow Cytometric Detection of CD59-Negative Peripheral Red Blood Cells and CD48-Negative Spleen T-Cells From the Rat", *Environ. Molec. Mutagen.* 49:614-621 (2008), a method for quantifying the frequency of mutant phenotype erythrocytes was identified. In that flow cytometry-based assay, anti-CD45 antibody was used to differentiate leukocytes from erythrocytes, and anti-CD59-FITC was used to distinguish mutant phenotype erythrocytes from wild-type erythrocytes. The authors also described a second approach whereby the fluorescent reagent FLAER and flow cytometry could be used to quantify the frequency of mutant phenotype erythrocytes. However, these approaches did not differentiate mature erythrocytes from the immature fraction of erythrocytes (reticulocytes). This is a significant disadvantage of the approach of Miura et al., because differential staining of mature and immature erythrocytes allows one to determine the percentage of reticulocytes among total erythrocytes simultaneously with Pig-A mutation measurements. These percent reticulocyte values provide important information regarding bone marrow toxicity, a parameter that is valuable for interpreting any genotoxicity endpoint that is based on hematopoietic cells. Differentially staining reticulocytes and mature erythrocytes also allows one to measure Pig-A mutation frequency in both the total RBC cohort as well as the reticulocyte fraction. The latter measurement is valuable for some experimental designs, since maximal mutagenic responses are obtained in this fraction of cells sooner than those observed in the total erythrocyte pool. Furthermore, the approach of Miura et al. for distinguishing erythrocytes from leukocytes was less than ideal. Namely, the use of anti-CD45 did not afford clear resolution of nucleated cells from erythrocytes. Rather than distinct populations, a continuum of CD45-associated fluorescent events was observed. The likely consequence of this is contamination of the erythrocyte analyses with leukocytes that failed to exhibit sufficient differential fluorescent resolution. This likely contributed to the report's somewhat high and variable baseline mutation frequencies.

In U.S. Patent Application Publ. No. 20070274919 to Derringer, a method of enumerating Pig-a mutation frequency from peripheral blood samples is identified. The described methodology uses a three-color labeling approach to distinguish GPI anchor-deficient cells from GPI anchor$^+$ cells, platelets from other blood cells, and reticulocytes from erythrocytes. It would be desirable, however, to obtain an assay that can achieve a reliable scoring method that requires fewer labeling reagents and is simpler to execute. Furthermore, it would be advantageous to utilize a method that is compatible with delayed quantitative analyses, because that would not only be more user-friendly but it would also allow sample preparation to occur at one site while quantitative analyses occur at a different site.

The present invention is directed to overcoming these and other deficiencies in the prior art.

DEFINITIONS

For purposes of the present invention, the following terms are defined as follows:

"PIG-A" and "Pig-A" are intended to mean the phosphatidylinositol glycan complementation group A gene. When referring to the human gene, the convention is to capitalize all letters, that is, PIG-A. When referring to other species, the convention is to use lower case letters, that is, pig-a. However, for the purposes of the present invention, the term Pig-A is meant to refer to any vertebrate species, including man.

"GPI" is intended to mean glycosylphosphatidylinositol, a glycolipid that is attached to the C-terminus of certain proteins during posttranslational modification. Certain GPI-anchored proteins such as CD24, CD59 and CD55 normally appear on the cell surface of erythrocytes.

"Erythrocytes" is intended to mean enucleated red blood cells, regardless of RNA content. Erythrocytes is abbreviated RBCs.

"Normochromatic erythrocytes" is intended to mean enucleated red blood cells that have matured to the point that RNA content is negligible. Normochromatic erythrocytes is abbreviated NCEs.

"Reticulocytes" is intended to mean recently formed enucleated red blood cells that are characterized by the presence of cytoplasmic RNA. Reticulocytes is abbreviated RETs.

"Pig-A mutant cells" is intended to mean erythrocytes and/or reticulocytes with altered Pig-A DNA sequence, such that transcription of the Pig-A gene is affected, resulting in a phenotype that is distinguishable by either a lack of or significant deficiency of GPI-anchored proteins on the cell surface.

"Expression time" is intended to mean the period of time following exposure of a DNA damaging event until the time that a mutated cell both expresses the GPI-anchor deficient phenotype and also appears in peripheral blood circulation.

SUMMARY OF THE INVENTION

A first aspect of the present invention relates to a method for the enumeration of in vivo Pig-A gene locus mutation. This method includes the steps of treating a peripheral blood sample, obtained from a mammal exposed to an exogenous agent, under conditions effective substantially to separate erythrocytes from platelets and leukocytes, thereby forming an enriched erythrocyte sample; first contacting the enriched erythrocyte sample with a first reagent that binds GPI anchor-expressing erythrocytes, but not GPI anchor-deficient erythrocytes, and that is conjugated to or can be bound by a first fluorochrome; second contacting the enriched erythrocyte sample with a second fluorescent reagent that differentially labels normochromatic erythrocytes from reticulocytes and leukocytes, the second fluorescent reagent having a fluorescent emission spectrum that does not substantially overlap with the fluorescent emission spectra of the first fluorochrome; exciting the first and second fluorochromes with light of appropriate excitation wavelength; and detecting the fluorescent emission and light scatter produced by erythrocytes labeled with the first fluorochrome, while excluding nucleated cells labeled by the second fluorochrome, and counting the number of GPI anchor-deficient erythrocytes and/or reticulocytes relative to the number of total erythrocytes or reticulocytes. With this specimen handling and gating strategy in place, it is possible to count the number of GPI anchor-deficient RBCs relative to the total number of RBCs, and/or the number of GPI anchor-deficient RETs relative to the number of total RETs.

A second aspect of the present invention relates to a method of assessing the DNA-damaging potential of an exogenous chemical agent. This method is carried out by exposing a mammal to an exogenous chemical agent, and then performing the method according to the first aspect of the present invention, wherein a significant deviation in the frequency of GPI-anchor-deficient RBCs or RETs from a baseline GPI-anchor-deficient RBC or RET frequency in unexposed or vehicle control mammals indicates the genotoxic potential of the exogenous chemical agent.

A third aspect of the present invention relates to a method of assessing the DNA-damaging potential of an exogenous physical agent. This method is carried out by exposing a mammal to an exogenous physical agent, and then performing the method according to the first aspect of the present invention, wherein a significant deviation in the frequency of GPI-anchor-deficient RBCs or RETs from a baseline GPI-anchor-deficient RBC or RET frequency in unexposed or sham-exposed control mammals indicates the genotoxic potential of the exogenous physical agent.

A fourth aspect of the present invention relates to a method of evaluating the effects of an exogenous agent that can modify endogenously-induced DNA damage. This method is carried out by administering to a mammal an exogenous agent that may modify endogenously-induced genetic damage; and then performing the flow cytometric method according to the first aspect of the present invention, wherein a significant deviation in the frequency of GPI-anchor-deficient RBCs or RETs from a baseline GPI-anchor-deficient RBC or RET frequency indicates that the exogenous agent can modify endogenous DNA damage.

A fifth aspect of the present invention relates to a method of evaluating the effects of an exogenous agent that can modify exogenously-induced DNA damage. This method is carried out by administering to a mammal a first exogenous agent that may modify exogenously-induced genetic damage; exposing the mammals to a second exogenous agent that causes genetic damage; and then performing the flow cytometric method according to the first aspect of the present invention, wherein a significant deviation in the frequency of GPI-anchor-deficient RBCs or RETs for genotoxicant-exposed mammals indicates that the first exogenous agent can modify exogenously-induced DNA damage.

A sixth aspect of the present invention relates to a kit that can be used to practice the methods of the present invention. The kit preferably includes a first reagent that binds GPI anchor-expressing cells, but not GPI anchor-deficient cells, and that is conjugated to or can be bound by a first fluorochrome; a second fluorescent reagent that differentially labels NCEs from RETs and leukocytes, the second fluorochrome having a fluorescent emission spectrum that does not substantially overlap with the fluorescent emission spectra of the first fluorochrome; a product suitable for substantial separation of RBCs from platelets and leukocytes; and optionally one or more of an instruction manual that describes blood processing as well as analysis procedures, an anticoagulant solution, one or more balanced salt solutions, and software templates that are useful for data acquisition and/or analysis.

As demonstrated herein, improved methods for enumerating Pig-A mutation frequency in blood specimens are described. The experimental results presented in the accompanying examples were conducted with CD-1 mice and Wistar Han rats. Two peripheral blood erythrocyte populations were evaluated for the GPI anchor-deficient phenotype: RBCs, and the newly formed immature fraction, RETs. As demonstrated by the accompanying examples, the present invention can achieve reliable, high-throughput scoring of in vivo mutations at the endogenous Pig-A gene locus using only two labeling reagents to discriminate between GPI anchor-deficient RBCs from total RBCs, and GPI anchor-deficient RETs from total RETs.

BRIEF DESCRIPTION OF THE DRAWINGS

FIGS. 3A-C illustrate three bivariate plots. Gated events (RBCs) are plotted on SYTO 13 (FL1, Y axis) versus anti-CD59-PE (FL2, X axis) bivariates. FIG. 3A illustrates the instrument calibration standard, which contains mutant-mimicking cells spiked into rat blood that was processed according to the standard protocol. This specimen provides enough negative and positive events to optimize PMT voltages and compensation settings. This calibration standard also represents a means for rationally and consistently setting the position of the vertical line that defines mutant versus non-mutant cells. FIG. 3B illustrates vehicle control rat blood, which is characterized by a very low incidence of cells that appear in the UL and LL quadrants. These anti-CD59-negative events are GPI anchor-deficient RETs and GPI anchor-deficient NCEs, respectively. FIG. 3C illustrates the analysis of a blood sample from a mutagen-treated rat. Note the elevated numbers of events that appear in the UL and LL quadrants, i.e., GPI anchor-deficient RETs and GPI anchor-deficient NCEs, respectively.

FIG. 7A shows dose-related increases to the frequency of mutant phenotype RBCs ($\times 10^{-6}$), whereas FIG. 7B shows dose-related increases to the frequency of mutant phenotype RETs ($\times 10^{-6}$).

DETAILED DESCRIPTION OF THE INVENTION

Figure 1:
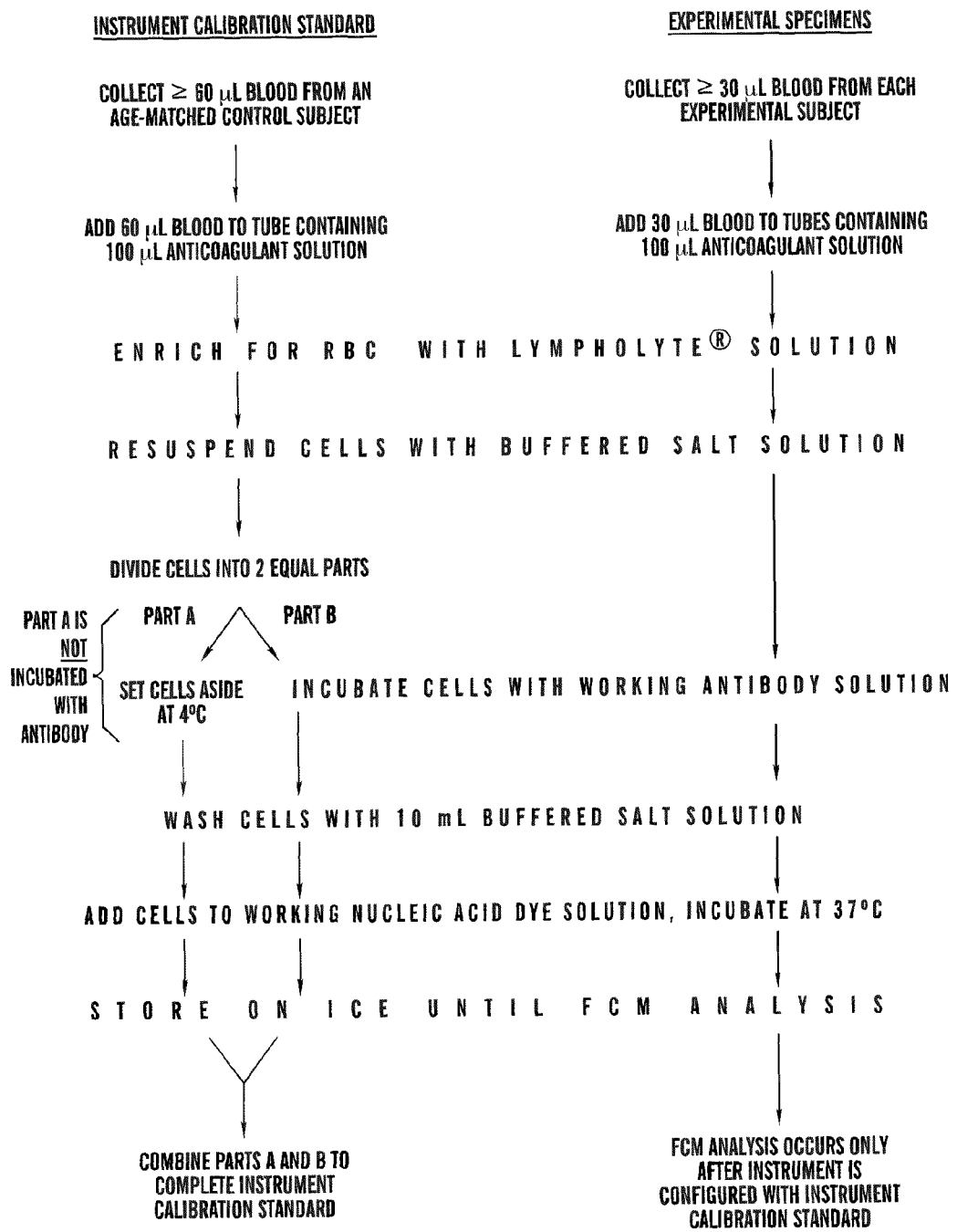
FIG. 1 illustrates a process for treating peripheral blood samples in accordance with one embodiment of the present invention.

The present invention is directed to methods and kits for the measurement of Pig-A mutant RBC and/or Pig-A mutant RET frequencies using an optical device designed for illumination and analysis of cell specimens.

The invention described herein provides for the measurement of Pig-A mutant frequency, preferably using flow cytometry technology. The advantageous characteristics of this invention relative to other in vivo mutation assays which have been reported to date are that it does not require transgenic animals, special breeding programs, or cell culture; and it is compatible with all mammalian species. Other advantages will become apparent in the discussion of the various embodiments.

With this method, blood specimens are obtained from mammals. If the exposure that one wishes to evaluate is acute, then a period of expression time is allowed to occur before samples are collected into an anticoagulant solution according to standard practices. If the exposure that one wishes to evaluate has been protracted, for instance as occurs for repeat dosing toxicity tests, then it will usually not be necessary to allow for a period of expression time before blood samples are collected. Alternatively, multiple samples can be collected over a period of time to monitor such long-term exposure.

Peripheral blood samples obtained from a subject are preferably treated in a manner effective substantially to separate RBCs from platelets and leukocytes. Preferably, the sample is enriched for RBCs such that leukocytes and platelets amount to less than about 0.01% of events per sample. One approach for achieving this degree of separation involves separation via centrifugation in an appropriate density gradient, e.g., Lympholyte® Mammal (Cedarlane Laboratories, Burlington, N.C.), which affords a cell pellet that can be resuspended, e.g., in balanced salt solution, to form an enriched RBC sample. Other commercially available density gradient products that can be used for this purpose exist, for instance Ficoll™ PM400 has a more than 30 year track record for blood cell separation procedures, and is based on a polysucrose and sodium diatrizoate formulation. Additional products include Ficoll-Paque PLUS™, Ficoll-Paque PREMIM™, Percoll™, and Percoll PLUS™. Whereas some of these products can be purchased at densities that are optimized for use with human blood (i.e., 1.077 g/mL), others have been optimized for mouse and rat blood (1.084 g/mL). Whatever reagent(s) are used for this purpose, the enriched RBC sample can then be treated in the manner described herein.

To achieve Pig-A mutant cell scoring according to the present invention, the enriched RBC sample is incubated with a reagent that binds to GPI-anchor competent (wild-type) cells, but not GPI-anchor deficient (Pig-A mutant) cells. By using a reagent that is either directly conjugated to a first fluorochrome, or else one that can be readily bound to a subsequently applied first fluorochrome, differential labeling of wild-type and mutant cells is achieved. Ideally, the specificity of the interaction is high, for instance that which is typically found with antibody-antigen interactions.

Preferred antibodies include, without limitation, first fluorochrome-conjugated anti-CD24 and/or anti-CD59 and/or anti-CD55, as well as mixtures thereof. Alternatively, these antibodies can be used in combination with secondary antibodies labeled with a first fluorochrome.

Alternately, the high affinity and specificity of the bacterial toxin aerolysin for the GPI anchor can also be used as a basis for differentially labeling wild-type and Pig-A mutant cells. For instance, a preferred embodiment includes contacting cells with a derivative of proaerolysin that binds to GPI anchors with high affinity, but does not lyse RBCs. This reagent is commercially available in a form that has been directly conjugated to a fluorochrome (FLAER™, available from Pinewood Scientific Services, Inc., Victoria, British Columbia), thus providing for direct labeling. Alternately, it is available as a biotinylated form (also from Pinewood), which provides for subsequent labeling with fluorochrome-conjugated avidin or streptavidin.

Subsequent to or concurrent with differential labeling of mutant versus wild-type cells, the enriched blood sample is contacted with a second fluorescent reagent. This second reagent is one that specifically binds to nucleic acids. By using a fluorescent reagent, or one that can be readily bound to a subsequently applied second fluorochrome, differential labeling of NCEs and RETs and leukocytes is achieved.

Exemplary second reagents include, without limitation, the nucleic acid dyes thiazole orange, SYTO® 13 dye, SYTO® 83 dye, and SYTO® RNASelect™ (all of which are cyanine dyes available from Invitrogen Corporation, Carlsbad, Calif.). Of these, SYTO® 13 dye is preferred.

While immunodetection reagents are described for use in the methods of the present invention, it should be appreciated that any suitable immunolabel can be used, including without limitation monoclonal antibodies, polyclonal antibodies, mono-specific polyclonal antibody preparations, chimeric antibodies, single chain antibodies, synthetic antibodies, and any antibody fragments, e.g., Fab fragments, Fab' fragments, $F(ab)_2$ fragments, $F(ab')_2$ fragments, Fd fragments, Fv fragments, dAb fragments, and isolated complementarity determining regions ("CDRs") (see U.S. Pat. Nos. 7,037,498, 7,034,121, 7,041,870, and 7,074,405, which are hereby incorporated by reference in their entirety). These antibody fragments can be made by conventional procedures, such as proteolytic fragmentation procedures, as described in J. Goding, *Monoclonal Antibodies: Principles and Practice*, pp. 98-118 (N.Y. Academic Press 1983), which is hereby incorporated by reference in its entirety. Methods for preparing antibodies that are specific to an analyte of interest are well known in the art. Conjugation of desired fluorochromes to antibodies is also well known in the art, and such immunoreagents are commercially available.

The various fluorochromes and nucleic acid dyes should be selected such that they can all be excited by the one or more light sources, yet their emission spectra are sufficiently distinct. Preferably, the emission maxima of the various fluorochromes and nucleic acid dyes do not substantially overlap (i.e., they have distinct emission maxima). With regard to their excitation spectra, it is preferable for the reagents to have similar excitation spectra because that affords the use of the more widespread single-laser flow cytometer.

Samples that have been contacted with two fluorescent reagents as described should be stored at about 4° C. and protected from light until ready for analysis. In a preferred embodiment of the present invention, samples are leukodepleted, stained, and analyzed on the same day of harvest. Alternately, the samples are leukodepleted and stored refrigerated until they can be stained and analyzed, preferably within approximately 48 hours of harvest.

Regardless of whether the samples are stained on the same day they are collected, or whether they have been stored and stained at a later date, the stained samples can be subjected to optical detection and enumeration of Pig-A mutant cells using any suitable optical detection system. Preferred optical detection systems have one or more light sources, preferably in the form of one or more amplified or collimated beams of light, that are able to excite the fluorescent reagents. Exemplary optical detection systems include, without limitation, single-laser flow cytometers and dual- or multiple-laser flow cytometers.

Single-laser flow cytometric analysis uses a single focused laser beam with an appropriate emission band to excite the several fluorescent reagents. As stained cells pass through the focused laser beam, they exhibit a fluorescent emission maxima characteristic of the fluorochromes or dyes associated therewith. The flow cytometer is equipped with appropriate detection devices to enable detection of the fluorescent emissions and light scatter produced by the cells. In this way, cell populations are counted and the frequency of reticulocytes and/or Pig-A mutant RBCs and/or Pig-A mutant RETs can be ascertained.

Dual- or multiple-laser flow cytometric analysis use two or more focused laser beams with appropriate emission bands, in much the same manner as described above for the single-laser flow cytometer. Different emission bands afforded by the two or more lasers allow for additional combinations of fluorescent dyes or immunochemical-conjugated fluorochromes to be employed.

The low frequency of Pig-A mutant cells in healthy mammals, for instance those that are untreated, sham-exposed or vehicle-treated, demands that a sensitive mutation scoring system be capable of interrogating at least several hundred cells per individual, but more ideally approximately $10^6$ cells per individual. This throughput is not particularly difficult when RBCs are considered. However, there are at least two reasons why there is merit in performing Pig-A mutation measurements in the RET fraction in addition to the total RBC pool.

One advantage of RET-based measurements is demonstrated by work with the peripheral blood cells of PNH patients. It has been shown that the number of circulating GPI-deficient neutrophils is typically higher than the number of affected RBCs. One explanation for this finding is that PNH RBCs are subject to complement-mediated intravascular lysis. Therefore, it is possible that an analytical system that focuses on the newly formed RETs would provide a more accurate mutation frequency. At least one previous report supports this view insofar as staining to identify RETs in the blood of PNH patients showed that the percentage of abnormal (GPI-deficient) RETs was similar to the percentage of affected neutrophils (Ware et al., "Immunophenotypic Analysis of Reticulocytes in Paroxysmal Nocturnal Hemoglobinuria," *Blood* 86:1586-1589 (1995), which is hereby incorporated by reference in its entirety). These data indicate that premature destruction of PNH RBCs may account for the fact that most patients have more GPI-deficient neutrophils than RBCs. Thus, a mutation assay based on RETs may be more sensitive than one based on total RBCs, especially if mutant RBCs exhibit a shortened lifespan.

It is important to note, however, that the specimens analyzed by Ware et al. were from PNH patients that expressed high frequencies of mutant RBCs, in the range of approximately 20 to 95%. These high frequencies are not found in non-PNH mammals, even following exposure to potent mutagens. Therefore, Ware et al. were not required to utilize a methodology that was capable of accurately enumerating GPI anchor-deficient cells at baseline and near-baseline frequencies, as is the case for a mutation assay system as described herein.

A second reason for studying Pig-A mutation in RETs is that this subpopulation would be expected to reflect genotoxicant-induced mutation more rapidly than the total RBC pool. That is, mutation frequency in the RET population would be expected to be a "leading indicator" of genotoxicant exposure. This temporal relationship reflects the fact that the spontaneous mutant frequency can only be affected by genotoxicant exposure after a sufficient length of time has elapsed, one that allows for a significant fraction of pre-existing (low mutation frequency) cells to be replaced by cells that exhibit an elevated mutation frequency. The time-frame for turning over blood RETs (days) is considerably shorter than for the total RBC pool (several weeks to about 4 months, depending on species), and is consequently expected to provide a quickly responding cohort, versus one that lags in time. Thus, shortening of mutant cell expression time is therefore a second advantage for studying Pig-A mutation in blood RETs.

While rapid interrogation of RETs is obviously desirable, their low incidence relative to total RBCs poses technical challenges. Despite the high throughput capacity of modern flow cytometers (often on the order of 7000 events per second), the interrogation of approximately $10^6$ RETs for mutation is time consuming. At this rate, a whole blood specimen with 3% RETs would require approximately 80 minutes to interrogate $10^6$ RETs. A second consideration is that data file sizes are extremely large when flow cytometric data for several hundred or more RETs per sample are acquired, and all the mature RBCs that accompany them are also saved to the same data file.

One solution to these obstacles is a thresholding technique, which involves use of (i) staining that distinguishes RETs from mature NCEs (e.g., SYTO® 13 dye), and (ii) an optical detection system whose threshold parameter is set for the nucleic acid dye-associated fluorescence channel (i.e., FL1 for SYTO® 13) rather than the more common forward scatter trigger. When set sufficiently high, taking into consideration differences in fluorescence intensities between mature and immature erythrocytes owing to differential staining, this can eliminate the mature erythrocytes from analysis. Finally, the specimen to be processed should be of sufficiently high density so as to reduce the acquisition time. Preferably the cell density is at least about $1\times10^8$ cells/ml; higher cell densities can produce faster acquisition rates.

One significant use of the present invention relates to genotoxicity assessment. In this case, an exogenous test agent is applied over a range of doses or intensities to mammals of interest. This test agent exposure may occur one or several times as is the case in acute or subacute toxicity tests, or repeatedly as is the case in subchronic and chronic toxicity tests. The test agent may be a chemical or formulation, or it could be a physical entity, such as the energy. Chemicals which are known to damage DNA include, but are not limited to: inorganic genotoxicants (e.g., arsenic, cadmium and nickel), organic genotoxicants (e.g., N-ethyl-N-nitrosourea, 4-nitroquinoline 1-oxide, etc.), anti-metabolites (e.g., 5-fluorouracil), organic genotoxicants that are generated by combustion processes (e.g., polycyclic aromatic hydrocarbons such as benzo(a)pyrene), as well as organic genotoxicants that are found in nature (e.g., aflatoxins such as aflatoxin B1). Examples of physical agents that are known to damage DNA include, but are not limited to: gamma radiation, neutron radiation, beta radiation, and UV radiation.

After an appropriate length of expression time which allows mutated bone marrow stem cells or erythroid progenitor cells to appear in peripheral blood as GPI-anchor deficient RETs or RBCs (i.e., from several days to several weeks post exposure), blood is harvested and prepared for flow cytometric enumeration of Pig-A mutants according to procedures outlined above and described in detail in the following examples.

Certain agents may offer protection from DNA damage, while others may magnify risk of damage. The present invention can also be used to evaluate the effects of an agent which can modify (i.e., enhance or suppress) such damage. To assess the suspected protective effects of an agent, mammals can be exposed to the putative protective agent either prior to, concurrently, or soon after exposure to a known genotoxicant. Any protective effect afforded by the agent can be measured relative to damage caused by the genotoxicant alone. Putative protective agents can be vitamins, bioflavonoids and antioxidants, dietary supplements (e.g., herbal supplements), or any other protective agent, whether naturally occurring or synthesized by man.

To assess the ability of an agent to synergistically or additively enhance genotoxicity, mammals can be exposed to the agent prior to, concurrently, or shortly after exposure to a known genotoxicant. Any additive or synergistic effect caused by the agent can be measured relative to damage caused by the genotoxicant alone.

The assays of the present invention can likewise be used to monitor chronic exposure to genotoxicant agents, for example, in individuals that work in environmental remediation, manufacturing industries that involve exposure to such agents, agricultural environments that involve pesticide or insecticide usage, etc. For these uses, period testing can be performed on a regular basis (e.g., weekly, monthly, quarterly, seasonally, biannually, etc.).

EXAMPLES

The examples below are intended to exemplify the practice of the present invention but are by no means intended to limit the scope thereof.

Example 1

Identification of Optimal Staining and Sample Preparation for In Vitro Samples

These in vivo experiments utilized naïve rats and focused on the development of simple and reproducible methods for staining and analyzing peripheral blood RBCs and RETs for the GPI anchor-deficient phenotype. As reported elsewhere, it was confirmed that the GPI-anchored protein CD59 is highly and stably expressed on RBCs throughout their lifespan in circulation (Hernández-Campo et al., "Quantitative Analysis of the Expression of Glycosylphosphatidylinositol-Anchored Proteins During the Maturation of Different Hematopoietic Cell Compartments of Normal Bone Marrow," *Cytometry* 72B:34-42 (2007), which is hereby incorporated by reference in its entirety). Furthermore, an anti-rat CD59 antibody was found to be commercially available. For the experiments described herein, CD59 was conjugated to PE, a fluorochrome that exhibits particularly high quantum efficiency. A second fluorescent reagent, SYTO® 13 dye, was chosen to differentially stain NCEs, RETs, and leukocytes. Whereas prior experiments had indicated that thiazole orange could serve this purpose, more recent work indicated that SYTO® 13 may be superior in at least two respects. Firstly, it provided a more stable fluorescence signal that did not shift over time, as was the case for thiazole orange. Secondly, it provided better fluorescent resolution between NCEs, RETs and blood leukocytes. The separation of these latter two populations is particularly important, because not all leukocytes express CD59, and these cells can therefore be mistaken for GPI anchor-deficient RBCs if they are not excluded from analysis. Early staining trials also included a third fluorescent reagent, anti-platelet antibody (biotinylated anti-CD61 plus streptavidin-Cy5-PE), which was added to positively identify platelets and prevent platelets from interfering with the RBC-centric analyses.

The prior three-color staining strategy outlined above has been described in Bryce et al., "In vivo mutation assay based on the endogenous Pig-a locus", *Environ. Molec. Mutagen.* 49:256-264 (2008) as well as U.S. Patent Application Publ. No. 20070274919 to Dertinger, each of which is hereby incorporated by reference in its entirety. That methodology appeared very promising, and resulted in very low mutation frequencies within the expected order of magnitude. Even so, the desire to simplify the flow cytometric scoring procedure resulted in the exploration of alternatives to the required anti-platelet reagent (i.e., for eliminating the anti-platelet reagent, if possible). Indeed, it was discovered that density gradient reagents, for instance products such as Lympholyte® Mammal (Cedarlane Laboratories, Ltd.), were sufficient substantially to eliminate platelets and leukocytes from the RBC pellet. Samples processed in this manner were evaluated with and without the anti-platelet antibody, and virtually identical values were consistently obtained. Thus, this blood handling/staining demonstrated that a relatively simple two-color labeling scheme was both suitable and preferable for the in vivo mutation assay (see FIG. 1).

Figure 2:
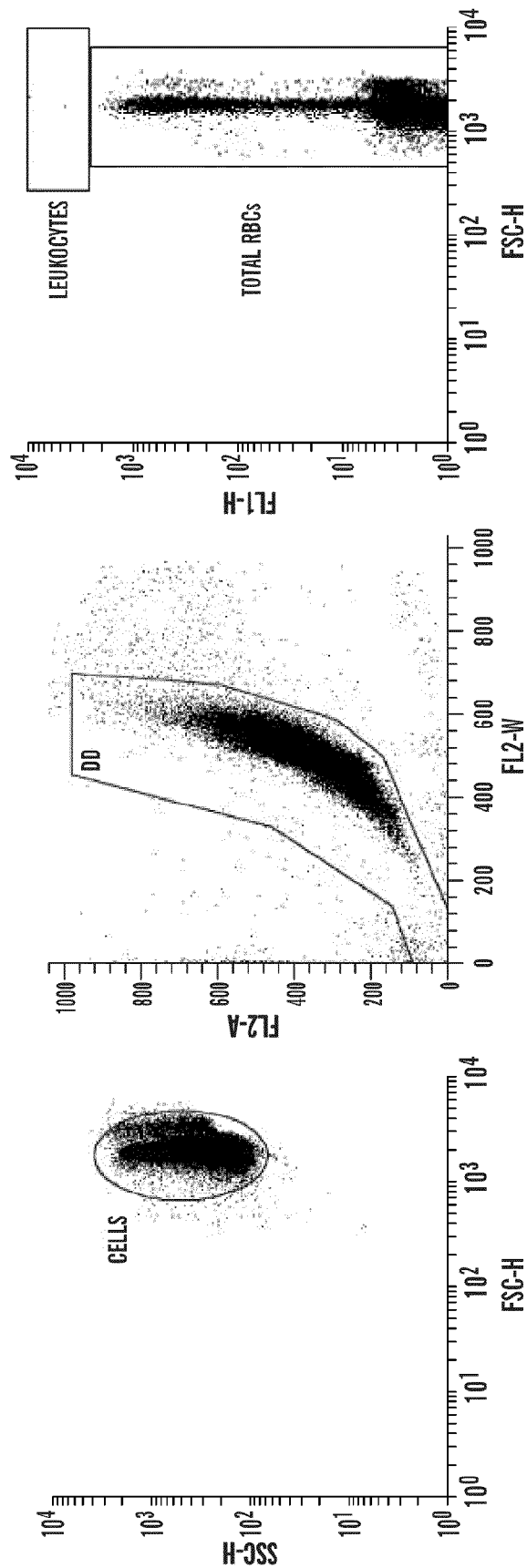
FIG. 2 illustrates three bivariate graphs that together show the gating logic used for the mutation scoring application described herein. Only events that fall within the "Cells", "DD" and "Total RBCs" regions are considered erythrocytes that should be evaluated for GPI anchored protein(s). Other events are excluded based on their failure to exhibit light scatter characteristics of cells (left panel) and/or their failure to fall within a region that is consistent with unaggregated and non-coincident particles (middle panel) and/or their high SYTO® 13 fluorescence intensity (right panel). Note that excluding events that exhibit very high SYTO® 13 or other nucleic acid dye associated fluorescence is important for eliminating nucleated cells (e.g., leukocytes) that may remain following erythrocyte enrichment procedure(s).

FIG. 2 illustrates the gating strategy that was devised to work in conjunction with the two-color labeling protocol for scoring GPI-anchor deficient erythrocyte populations. The right panel illustrates the SYTO® 13 fluorescence profile (Y axis) that is exhibited by NCEs versus RETs versus residual leukocytes. Whereas Lympholyte® separation eliminated the vast majority of leukocytes, it was found that to achieve reliable erythrocyte analyses it is particularly important to have a staining strategy in place that helps to exclude the rare contaminating nucleated cells (which would otherwise skew results if not properly excluded).

Gated events (total RBCs) are then applied to a SYTO® 13 versus anti-CD59-PE bivariate graph as illustrated in FIGS. 3A-C. In addition to showing representative blood from vehicle control and mutagen-treated rats, these figures also demonstrate the use of a biological calibration standard. That is, before each day of analysis, the flow cytometer settings are configured for this rare event scoring application by running a specimen that has been stained according to the standard protocol, but also has mutant-mimicking RBCs spiked in (FIG. 3A). These mutant mimics are generated through the substitution of purified anti-CD59 for the PE-conjugate, or else by refraining from contacting a portion of the blood cells with the antibody reagent as outlined in FIG. 1. The highly elevated numbers of these mutant RBCs enhances the operator's ability to optimize PMT voltage and compensation settings. Furthermore, this specimen provides a rational and consistent means for setting the vertical demarcation line that is used to distinguish wild-type from mutant RBCs.

Optimization of the staining strategy and confirmation of adequate fluorescent resolution were important considerations for this rare event scoring application. Even so, before moving on to in vivo rodent experiments that involved administrations of mutagenic chemicals, the analytical performance of the method was critically evaluated. This was initially addressed by reconstruction experiments whereby blood from naïve rats was collected and RBCs were isolated via Lympholyte® separation. The cells were washed and then stained according to a two-color staining protocol (e.g., anti-CD59-PE and SYTO® 13). In parallel with these specimens, a fraction of blood was stained with SYTO® 13, but was not incubated with anti-CD59-PE. As described above, this is useful for optimizing instrument settings each day of analysis. For this experiment, these mutant-mimicking cells served another purpose, and that was to test the analytical performance of the method. For these experiments, mutant mimicking cells were spiked into a tube containing blood cells from a naïve rat that underwent the standard staining protocol. This "High Mutant Frequency" preparation was then serially diluted with additional blood from the naïve rat that underwent the standard staining protocol. In this manner, it was possible to prepare specimens with a range of mutant frequencies and compare observed mutant frequencies obtained through flow cytometric analysis with those that were expected. Representative data are shown in Table I below. The analytical system's ability to serve as a mutant scoring assay was supported by observations that expected values are consistently in very good agreement with observed values, even for specimens that have fewer than 100 mutant cells added per $10^6$ RBCs.

TABLE I

Representative Results of a Reconstruction Experiment

| Specimen | Dilution | Observed Mutant RBC Frequency ($\times 10^{-6}$) | Expected Mutant RBC Frequency ($\times 10^{-6}$) |
|---|---|---|---|
| High Mutant Frequency | | 45216 | |
| Spike 1 | 1:9 | 4660 | 4522 |
| Spike 2 | 1:99 | 435 | 452 |
| Spike 3 | 1:999 | 37 | 45 |
| Naïve Control | | 0 | |

Reconstruction experiments, such as the one described above, demonstrated that reliable scoring of baseline and near-baseline Pig-A mutant frequencies demands an analytical scoring system that is capable of interrogating several hundred thousand cells per rodent, preferably on the order of $10^6$ cells. It is not particularly challenging to accomplish this when total RBCs are considered. However, there are at least two reasons why there is merit to performing Pig-A mutation measurements in the RET fraction in addition to the total RBC pool, and this poses challenges to rapid data acquisition.

While the interrogation of RETs would seem desirable, their low incidence relative to total RBCs poses technical challenges. Despite the high throughput capacity of modern flow cytometers (usually on the order of 7000 events per second), the interrogation of approximately $10^6$ RETs for mutation is time consuming. At this rate, a whole blood specimen with 3% RETs would require approximately 80 minutes to interrogate $10^6$ RETs. A "thresholding technique," described below, allows these analyses to be performed in a fraction of this time.

Figure 4A:
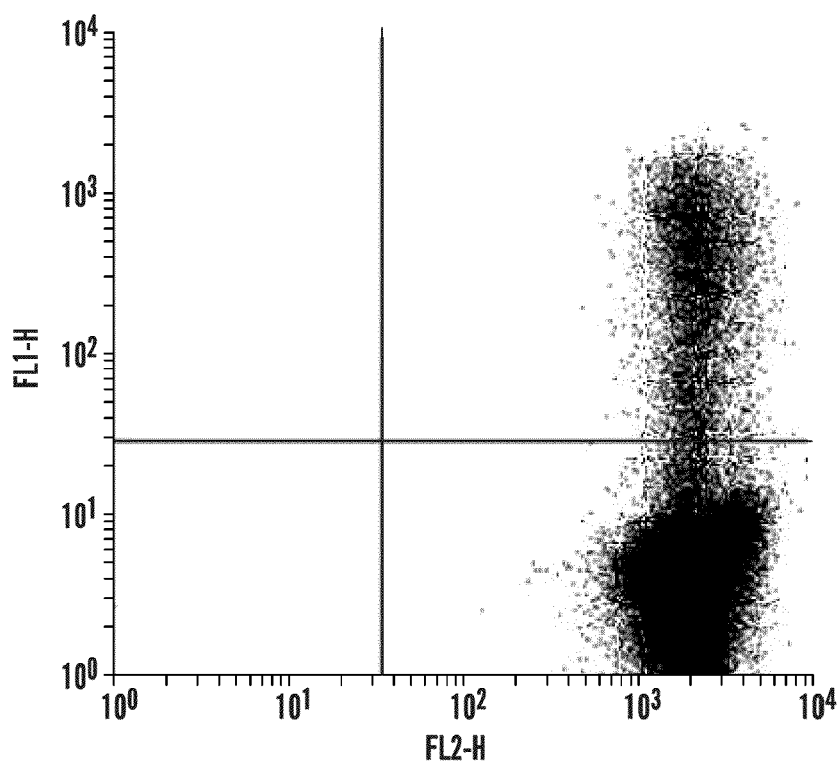
FIGS. 4A-B are a pair of bivariate plots that illustrate analyses based on FSC thresholding (FIG. 4A) and nucleic acid dye fluorescence thresholding (FL1 in the case of SYTO® 13 dye) (FIG. 4B). FSC thresholding is capable of efficiently evaluating $10^6$ or more total RBCs for the mutant phenotype. The plot of FIG. 4B was generated using FL1 thresholding (SYTO® 13 fluorescence intensity). This strategy enables efficient evaluation of hundreds of thousands of RETs per specimen.
Figure 4B:
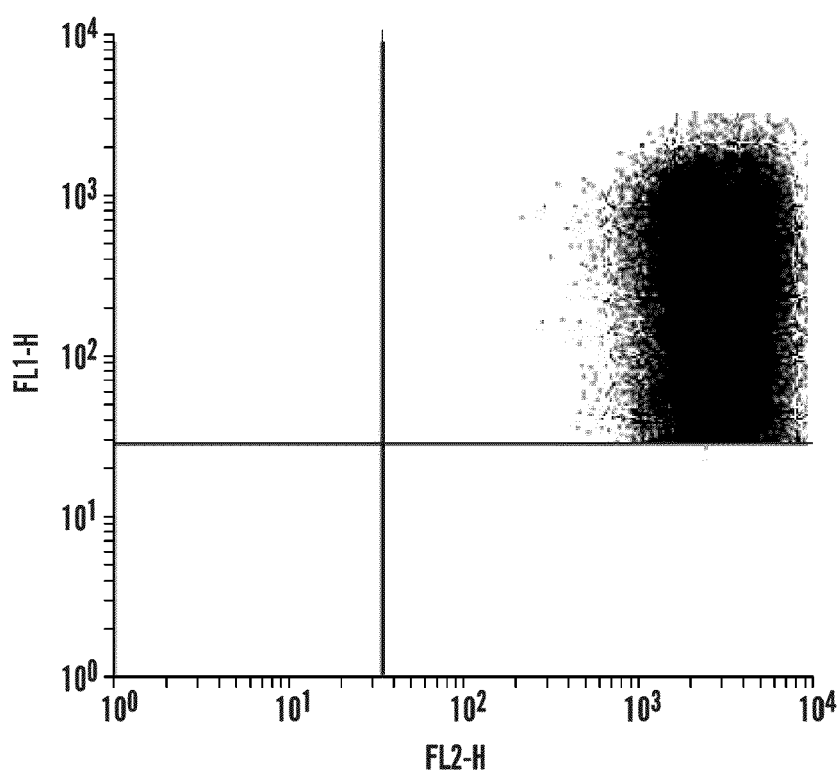

The thresholding technique is based on the fact that the vast majority of Lympholyte® processed blood cells are mature RBCs. With appropriate staining (e.g., SYTO® 13), it is possible to distinguish RETs from their more mature counterparts (FIGS. 3A-C). In this case, it is possible to set the threshold parameter to the nucleic acid dye-associated fluorescence channel (i.e., FL1 for SYTO® 13), as opposed to the more common forward scatter trigger. When set sufficiently high, this can eliminate NCEs from analysis (see FIGS. 4A-B). Of course, fluorescence thresholding alone does not improve RET interrogation rates. Rather, it must be coupled with the preparation of relatively high density specimens. When these two adjustments are made, much quicker data acquisition rates are achieved. For instance, by eliminating mature RBCs with an FL1 threshold and analyzing specimens prepared at relatively high cell densities (as high as $2 \times 10^8$/ml), it was possible to reduce the time needed to acquire $10^6$ RETs from 80 minutes to about 10 to 15 minutes. In practice, this means that when one desires to measure the frequency of both mutant phenotype RBCs and mutant phenotype RETs, each specimen should be analyzed two times: once at a low sample rate and FSC thresholding, and a second time at a high sample rate and FL1 thresholding. In this manner, it is possible to efficiently interrogate $10^6$ total RBCs and several hundred thousand RETs for the mutant phenotype.

Example 2

In Vivo Responses to Mutagens in ENU-Treated Rats

With a stable protocol in place for efficiently interrogating $10^6$ total RBCs and hundreds of thousands of RETs for the mutant phenotype, experiments with 7-8 week old male Wistar rats were initiated.

For this study, rats were treated on three consecutive days (Days 1, 2, and 3) with N-ethyl-N-nitrosourea (ENU) via oral gavage. The dose levels were 0, 20 or 40 mg/kg/day (n=5 per group). Serial blood specimens were collected before treatment (Day −1), as well as on Days 4, 15, 30, 45 and 90. There are three primary endpoints derived from flow cytometric analyses as described herein, and each will be described in turn.

Figure 5A:
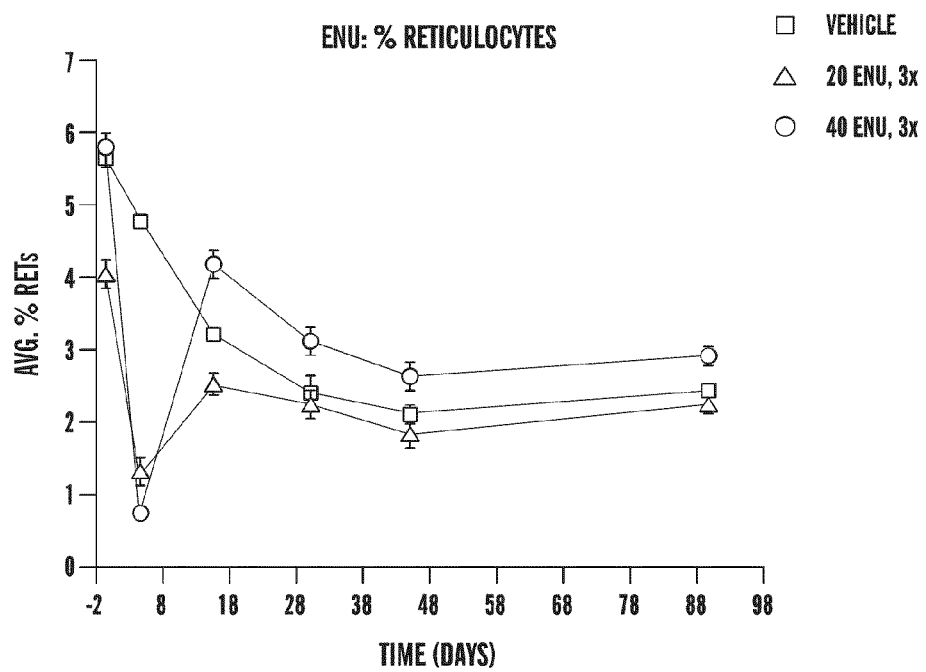
FIGS. 5A-C are graphs showing time-course data for rats treated for three consecutive days with the mutagen N-ethyl-N-nitrosourea (ENU, 0, 20, or 40 mg/kg/day). Each graph illustrates one of the three endpoints that are acquired with the present invention: the frequency of reticulocytes (% RET) (FIG. 5A), the frequency of mutant phenotype RBCs ($\times 10^{-6}$) (FIG. 5B), and frequency of mutant phenotype RETs ($\times 10^{-6}$) (FIG. 5C).

One endpoint that is obtained from analyses based on a forward light scatter threshold is the frequency of reticulocytes (% RET). This statistic is obtained expressing the number of RNA-containing erythrocytes (i.e., SYTO® 13 or other nucleic acid dye positive erythrocytes) as a percentage of the total number of erythrocytes scored. This endpoint reflects erythropoiesis function, and is valuable for monitoring the degree to which test subjects' bone marrow compartment is affected by treatment. In this example, vehicle control % RET values are observed to decrease over time (see FIG. 5A). Even so, an ENU-induced toxic effect whereby mean % RET are reduced in a dose-dependent manner is also apparent. As is common with potent toxicants, a rebound effect is evident for the high dose group whereby the mean % RET actually "overshoots" the control values as the rats attempt to compensate for toxicity occurring to the bone marrow compartment.

Figure 5B:
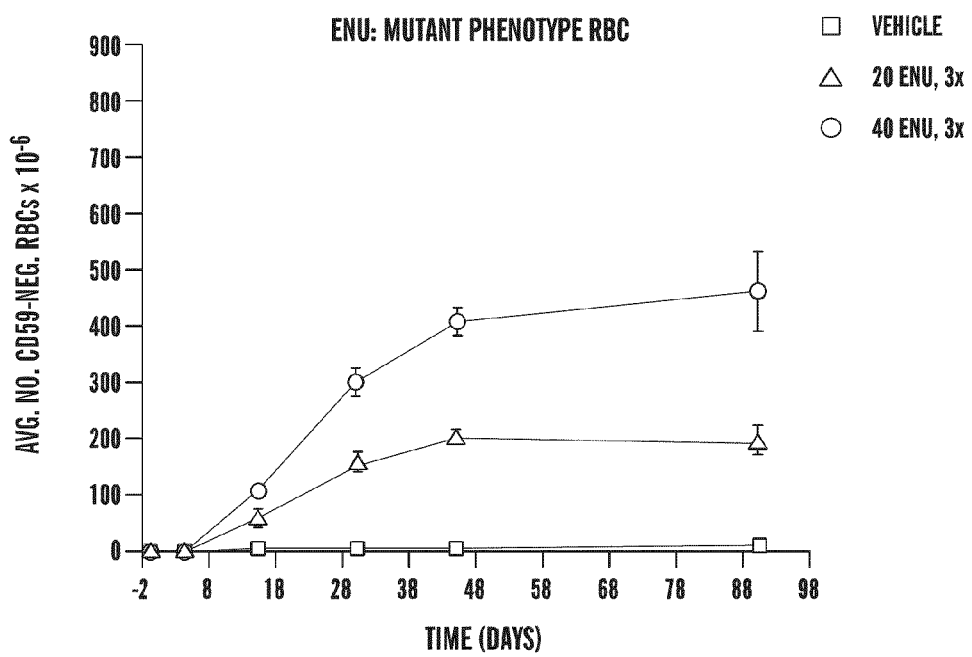

A second endpoint is obtained from the analyses based on a forward light scatter threshold: the frequency of GPI anchor-deficient RBCs. This value is captured by the present invention by enumerating the number of GPI anchor-deficient RBCs and the number of total RBCs. The GPI anchor-deficient RBC value is then expressed as a frequency, usually per $10^6$. Mutant RBC frequency data for the ENU experiment are presented in FIG. 5B. Robust, dose-related increases in mutant cell frequency are evident from Day 15 through Day 90. Maximal values are reached by Day 45, with an apparent plateau thereafter. The persistence of the effect so many days after treatment has two important implications. First, it indicates that it is hematopoietic stem cells and/or other populations of cells with a prolonged self-renewal capacity that are the targets of Pig-A mutation, at least for some chemicals. Secondly, it provides evidence that the bone marrow stem cells and/or progenitors that have acquired Pig-A mutations are not severely selected against in vivo. Otherwise, the mutation frequency values would have changed over time. This characteristic implies that Pig-A mutations are "neutral", and adds strong support to the premise that a sensitive mutation assay can be built around this locus. Others have reported on murine models of PNH, and provide additional evidence that bone marrow stem cells and/or early progenitors that are Pig-a mutant are neither selected against, nor exhibit a marked growth advantage (Keller et al., "X Inactivation and Somatic Cell Selection Rescue Female Mice Carrying a PigA-null Mutation," *Proc Natl Acad Sci USA* 96:7479-7483 (1999); Rosti, "Murine Models of Paroxysmal Nocturnal Hemoglobinurea," *Ann NY Acad Sci* 963:290-296 (2002), each of which is hereby incorporated by reference in its entirety).

Figure 5C:
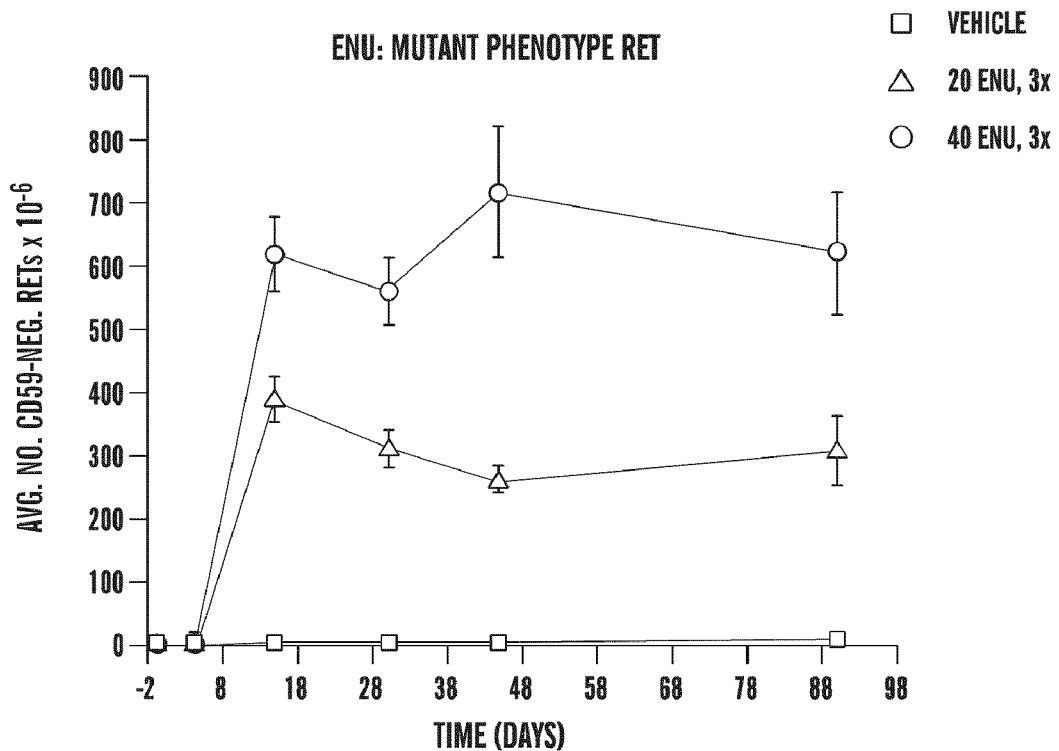

A third endpoint is obtained from the analyses based on SYTO® 13 or another nucleic acid dye fluorescence: the frequency of GPI anchor-deficient RETs. This value is captured by the present invention by enumerating the number of GPI anchor-deficient RETs and the number of total RETs. The GPI anchor-deficient RET value is then expressed as a frequency, usually per $10^6$. Mutant RET frequency data for the ENU experiment are presented in FIG. 5C. Robust, dose-related increases in mutant cell frequency are evident by Day 15, where a maximal or near-maximal value is reached. The maximal response occurs sooner than that in the total RBC population, as the turn-over of pre-existing (predominately wild-type) RETs occurs much faster than the total RBC pool. The persistence of the effect noted in the total RBC population is corroborated by these mutant RET data, again indicating that hematopoietic stem cells and/or other populations of cells with a prolonged self-renewal capacity that are the targets of pig-a mutation, at least for some chemicals. Interestingly, the frequency of mutant phenotype RETs is always somewhat greater than the frequency of mutant phenotype RBCs. It is believed, therefore, that mutant phenotype erythrocytes have a slightly reduced lifespan in circulation relative to wild-type erythrocytes, thereby slightly muting the mutation frequencies observed in the total RBC cohort relative to the immature fraction that only recently entered peripheral blood circulation.

Example 3

In Vivo Responses to Mutagens in DMBA-Treated Rats

For this study, rats were treated on three consecutive days (Day 1, 2 and 3) with 1,2-benz[a]anthracene (DMBA) via oral gavage. The dose levels were 0, 25 or 50 mg/kg/day (n=5 per group). Serial blood specimens were collected before treatment (Day −1), as well as on Days 4, 15, 30, 45 and 90.

Figure 6A:
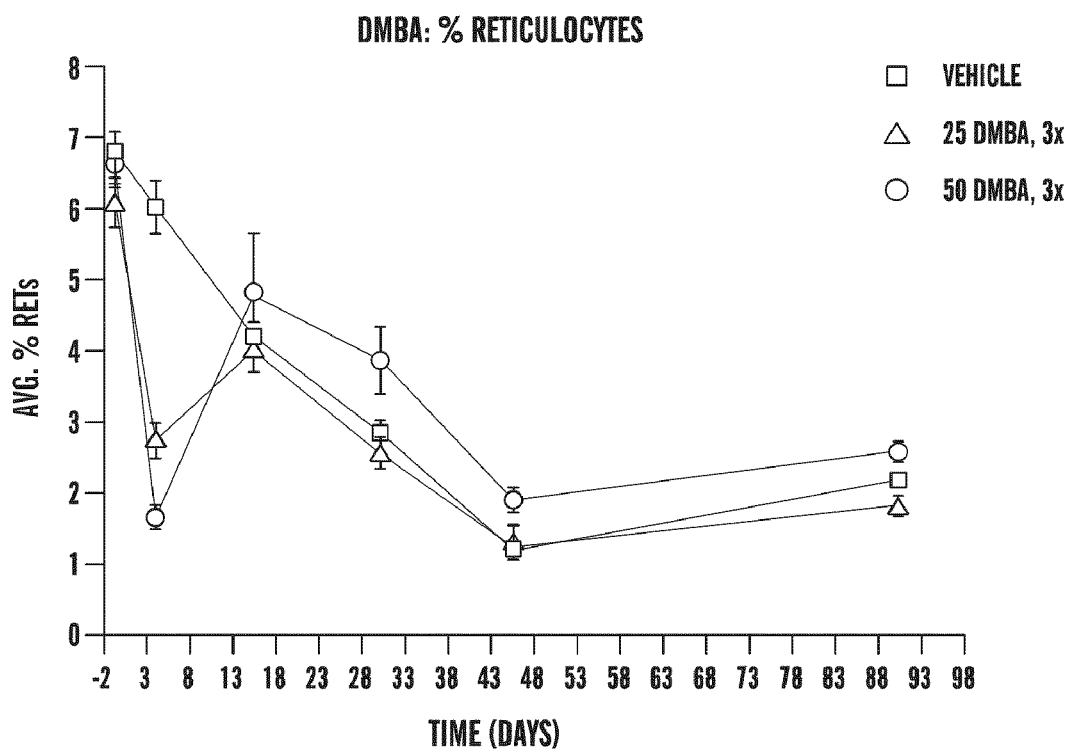
FIGS. 6A-C are graphs showing time-course data for rats treated for three consecutive days with the mutagen 1,2-benz [a]anthracene (DMBA, 0, 25 or 50 mg/kg/day). Each graph illustrates one of the three endpoints that are acquired with the present invention: the frequency of reticulocytes (% RET) (FIG. 6A), the frequency of mutant phenotype RBCs ($\times 10^{-6}$) (FIG. 6B), and frequency of mutant phenotype RETs ($\times 10^{-6}$) (FIG. 6C).

Vehicle control % RET values were observed to decrease over time (see FIG. 6A). Even so, a DMBA-induced toxic effect, whereby mean % RET are reduced in a dose-dependent manner, is also apparent. As is common with potent toxicants, a rebound effect is evident for the high dose group whereby the mean % RET actually "overshoots" the control values as the rats attempt to compensate for toxicity occurring to the bone marrow compartment.

Figure 6B:
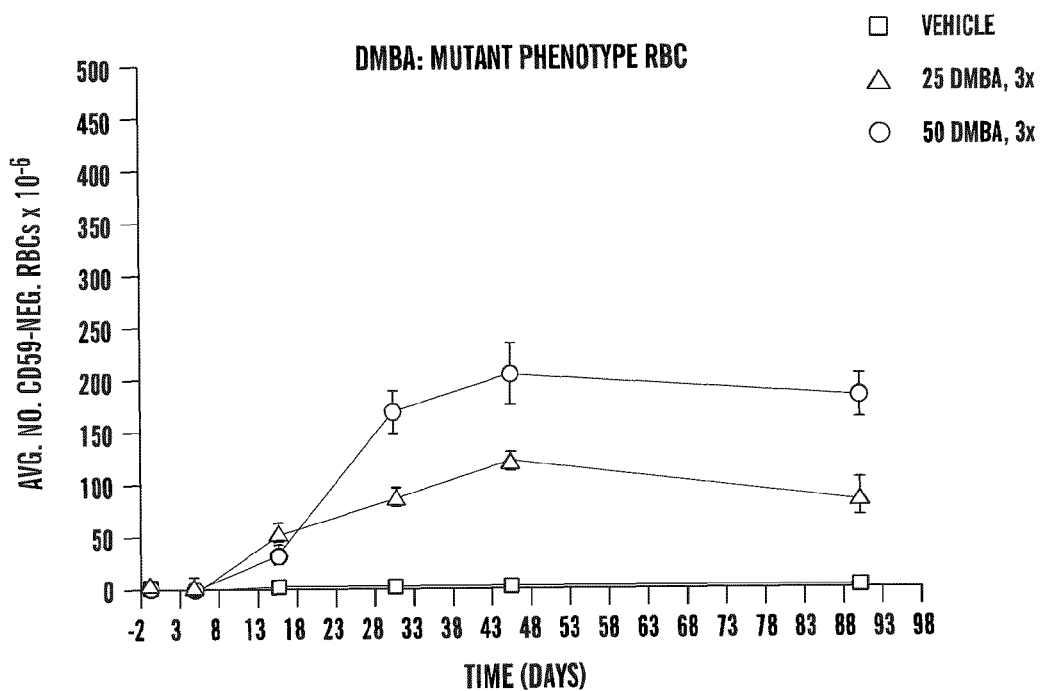

Mutant RBC frequency data for the DMBA experiment are presented in FIG. 6B. Robust increases in mutant cell frequency are evident from Day 15 through Day 90. Maximal values are reached by Day 45, which is consistent with the life-span of circulating rat erythrocytes. As with ENU, the persistence of the effect so many days after indicates that cells with prolonged self-renewal capacity are targets of Pig-A mutation, at least for some chemicals.

Figure 6C:
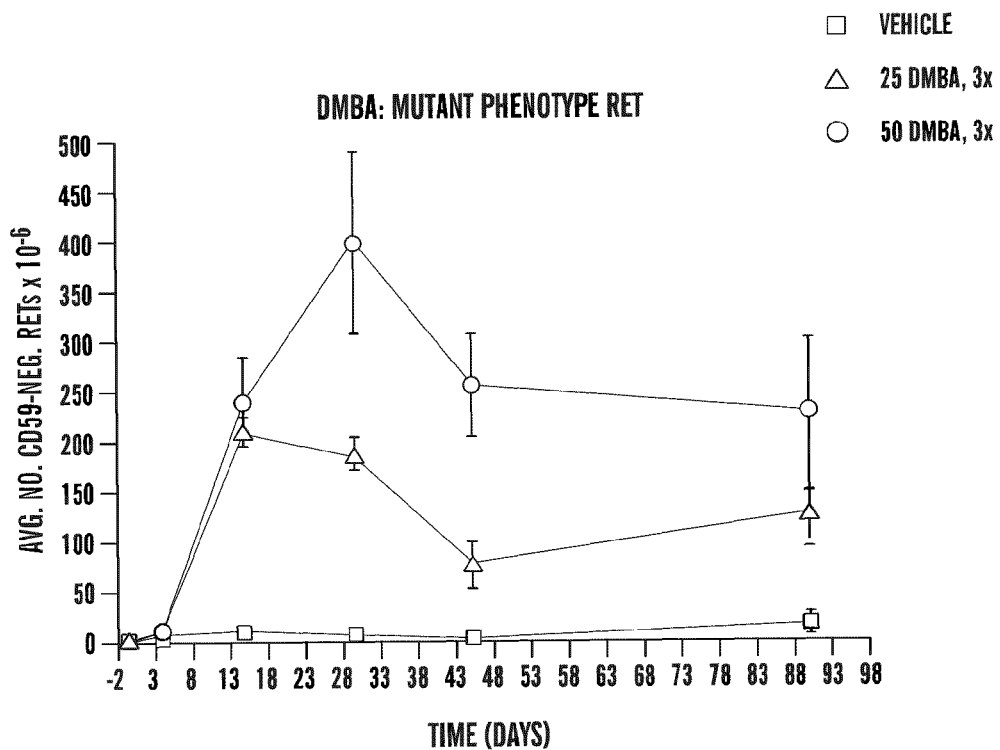

Mutant RET frequency data for the DMBA experiment are presented in FIG. 6C. Robust increases in mutant cell frequency are evident from Day 15 through Day 90. Maximal or near-maximal values are reached between Days 15 and 30. Interestingly, there is a modest reduction to mutant frequency RETs between Day 30 and 45. This decrease may reflect the loss of mutant erythroid progenitors or else short-term hematopoietic stem cells that do not have an indefinite capacity to self-renew.

Example 4

In Vivo Responses to Mutagens in Protractedly Exposed Rats

The potential of this assay to study exposures that involve protracted administration of a test article, for instance as occurs for repeat-dosing toxicology studies, is illustrated in this example whereby male Wistar rats were treated on fourteen consecutive days with N-ethyl-N-nitrosourea (ENU) via oral gavage. The dose levels were 0, 1, 5, 10 or 15 mg/kg/day (n=4 for vehicle controls, n=2 per ENU dose level). Blood specimens were collected and analyzed according to the present invention on Day 23.

Figure 7A:
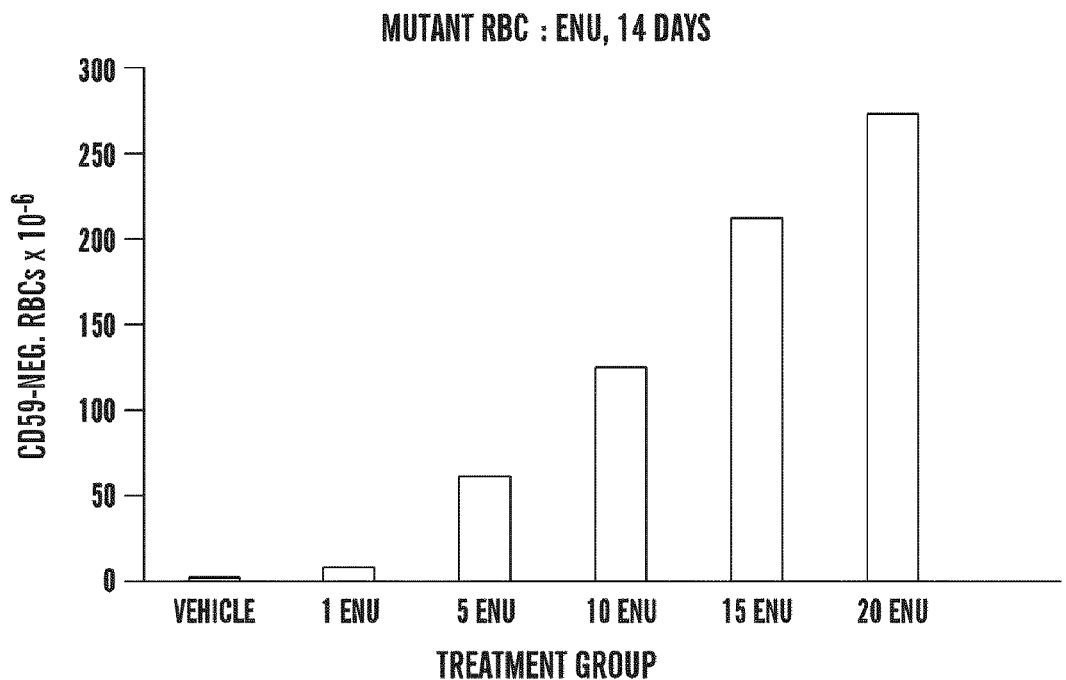
FIGS. 7A-B are graphs that show the dose response relationship for two endpoints that are acquired with the present invention following protracted exposure of rats to the mutagen N-ethyl-N-nitrosourea (ENU, 14 consecutive days of exposure).
Figure 7B:
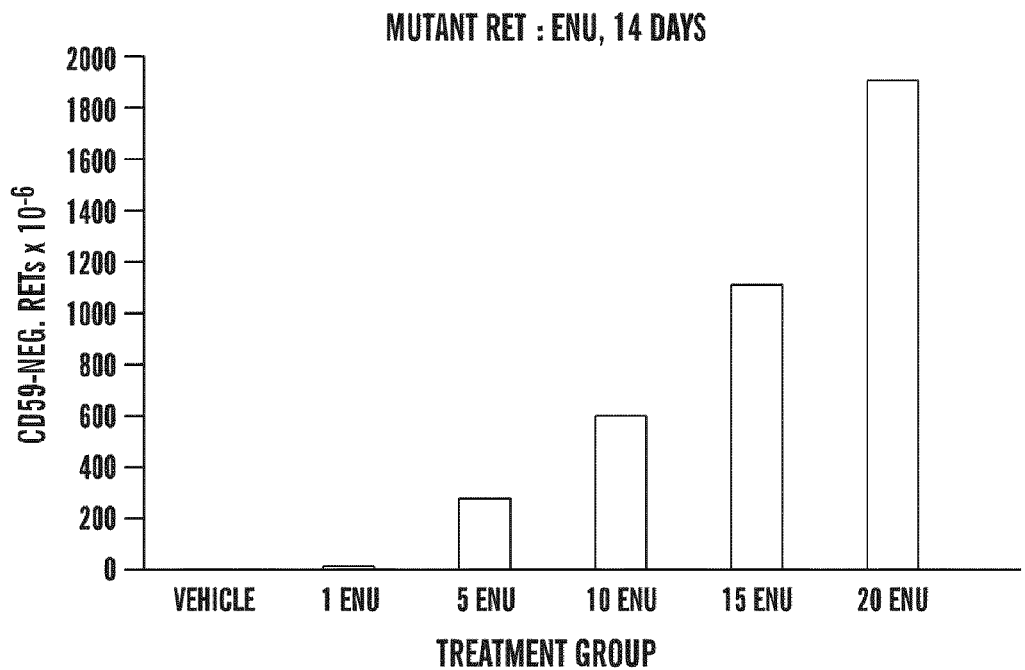

Mutant RBC frequency data and mutant RET frequency data are presented in FIGS. 7A and 7B, respectively. In each cohort of erythrocytes, a very robust, dose-related increase in mutant cells is evident. The effect is most pronounced in the RET subpopulation, a finding that is predicted based on the time-course data described in Example 2, as well as the life-span of erythrocytes in circulation. Interestingly, the ENU genotoxic effect is evident over the entire range of concentrations studied (20-fold difference between low and high dose). This is unusual for a genetic toxicology assay, as many endpoints such as micronucleus formation are expressed over a rather narrow range of dose levels. This is one advantage of the invention described herein.

Example 5

In Vivo Responses to Mutagens in ENU-Treated Mice

The cross-species potential of this assay is illustrated by this example, whereby male CD-1 mice were treated on three consecutive days (Day 1, 2 and 3) with N-ethyl-N-nitrosourea (ENU) via oral gavage. The dose levels were 0 or 40 mg/kg/day. Blood harvests occurred on Days 4, 15, 30, 45 and 90 (n=5 per time point per dose). Whereas the rat experiments described in Examples 2-4 above were based on serial blood draws, the mouse experiments were not. Rather, each mouse provided only one blood specimen, thereby requiring like-treated groups of animals to generate the data for each time point studied. This was done to eliminate the possible confounding effect that repeat-blood sampling may have had on the results given the low total blood volume associated with this particular small animal model.

Figure 8A:
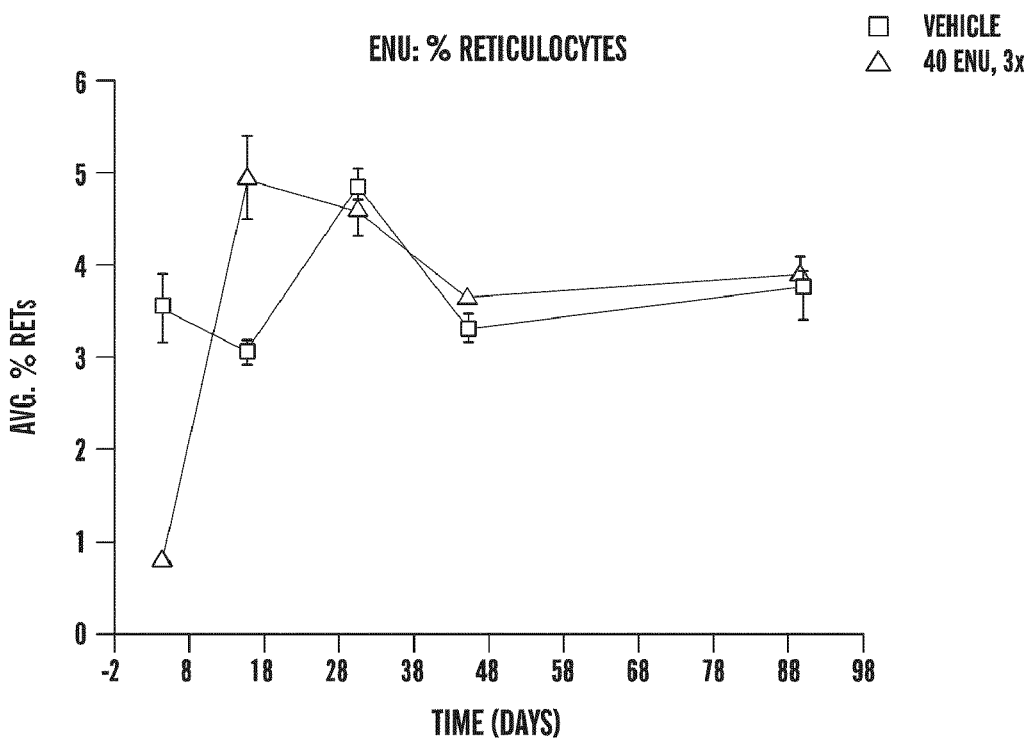
FIGS. 8A-C are graphs showing time-course data for mice treated for three consecutive days with vehicle or the mutagen N-ethyl-N-nitrosourea (ENU, 40 mg/kg/day). Each graph illustrates one of the three endpoints that are acquired with the present invention: the frequency of reticulocytes (% RET) (FIG. 8A), the frequency of mutant phenotype RBCs ($\times 10^{-6}$) (FIG. 8B), and frequency of mutant phenotype RETs ($\times 10^{-6}$) (FIG. 8C).

Vehicle control % RET values are observed to fluctuate moderately over time (see FIG. 8A). Even so, an ENU-induced toxic effect whereby mean % RET as significantly reduced on Day 4 is also apparent. As is common with potent toxicants, a rebound effect is evident at the Day 15 time-point whereby the mean % RET actually "overshoots" the control values as the mice attempt to compensate for toxicity occurring to the bone marrow compartment.

Figure 8B:
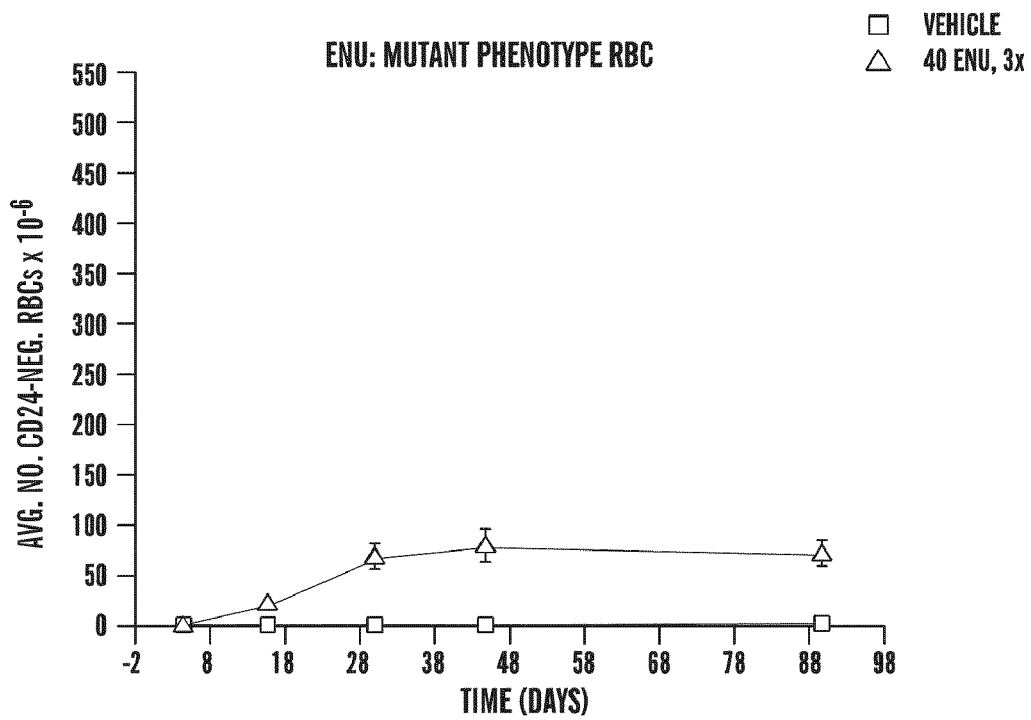

Mutant RBC frequency data for the ENU experiment are presented in FIG. 8B. While increased mutant cell frequencies are evident by Day 15, a maximum value is not apparent until the Day 30 time-point. From this time forward, the mutant frequencies are observed to stabilize through Day 90, the last time-point considered. As with ENU-treated rats, the persistence of the effect so many days after treatment indicates that cells with prolonged self-renewal capacity are targets of Pig-A mutation, at least for some chemicals.

Figure 8C:
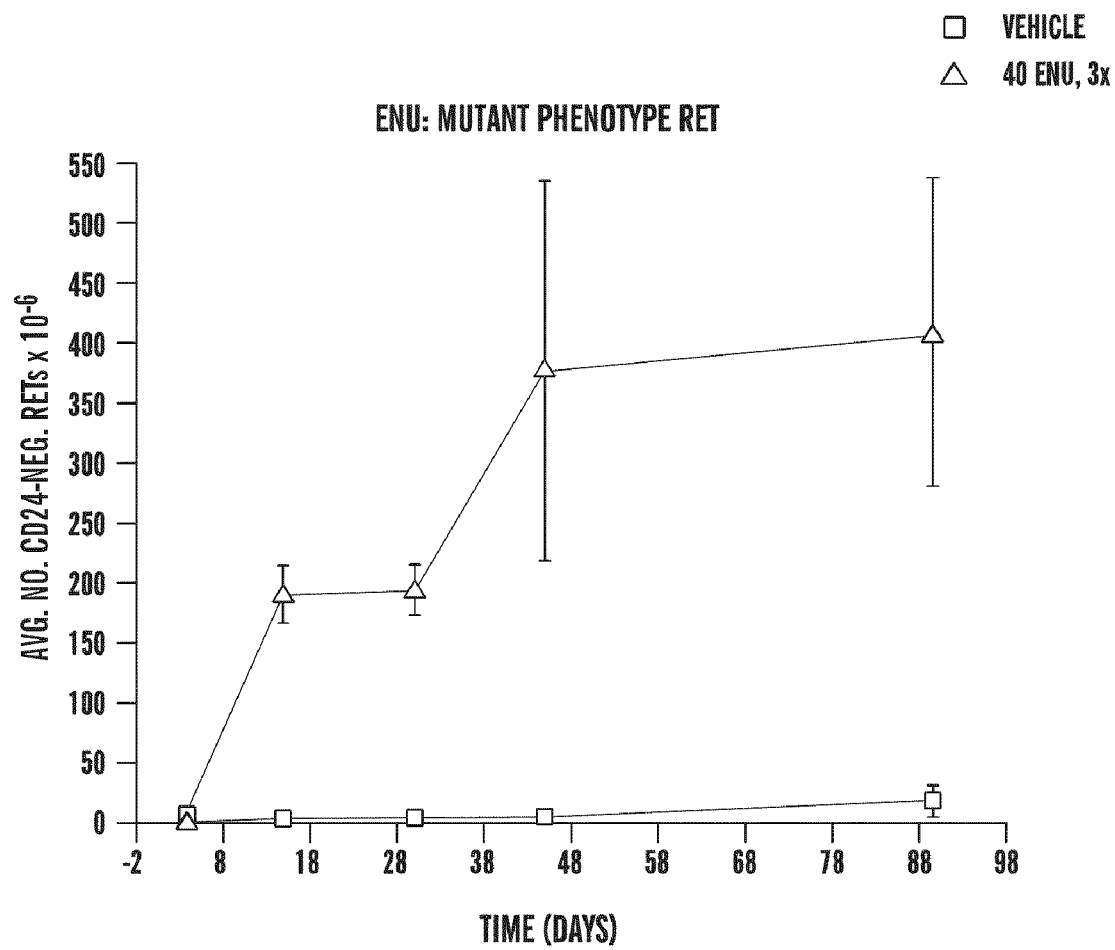

Mutant RET frequency data for the ENU experiment are presented in FIG. 8c. Whereas the response was modest on Day 15 when the RBC cohort was considered, the mutant RET frequency was greatly elevated at this time. Robust increases in mutant cell frequency continue through Day 90, again indicating that cells with substantial self-renewal capacity are targets of Pig-A mutation, at least in the case of ENU.

Example 6

Effective Storage of Blood Specimens

It is not always convenient or possible to quantitatively analyze blood samples on the same day that harvest occurs. A preferred approach for storing these samples prior to analysis is described. With this approach, analysis can be delayed for at least 2 days, providing the assay with greater logistical flexibility.

Figure 9A:
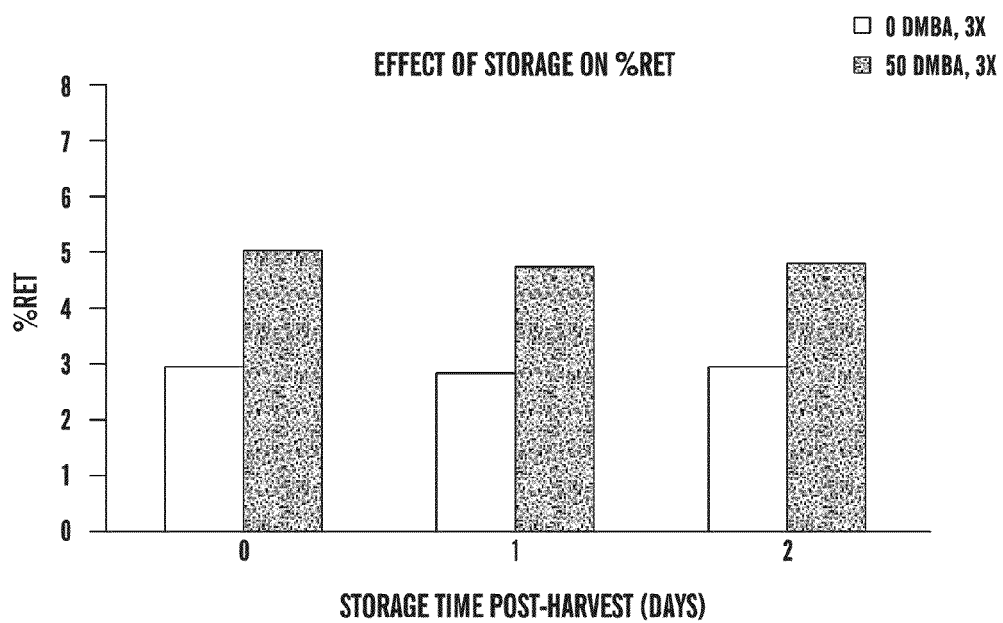
FIGS. 9A-C are graphs showing the lack of substantial effect of storing leukodepleted and refrigerated blood on each of the endpoints acquired with the present invention: the frequency of reticulocytes (% RET) (FIG. 9A), the frequency of mutant phenotype RBCs ($\times 10^{-6}$) (FIG. 9B), and frequency of mutant phenotype RETs ($\times 10^{-6}$) (FIG. 9C). Day 0 corresponds to the same day blood was collected, whereas Days 1 and 2 represent one and two days of storage, respectively.
Figure 9B:
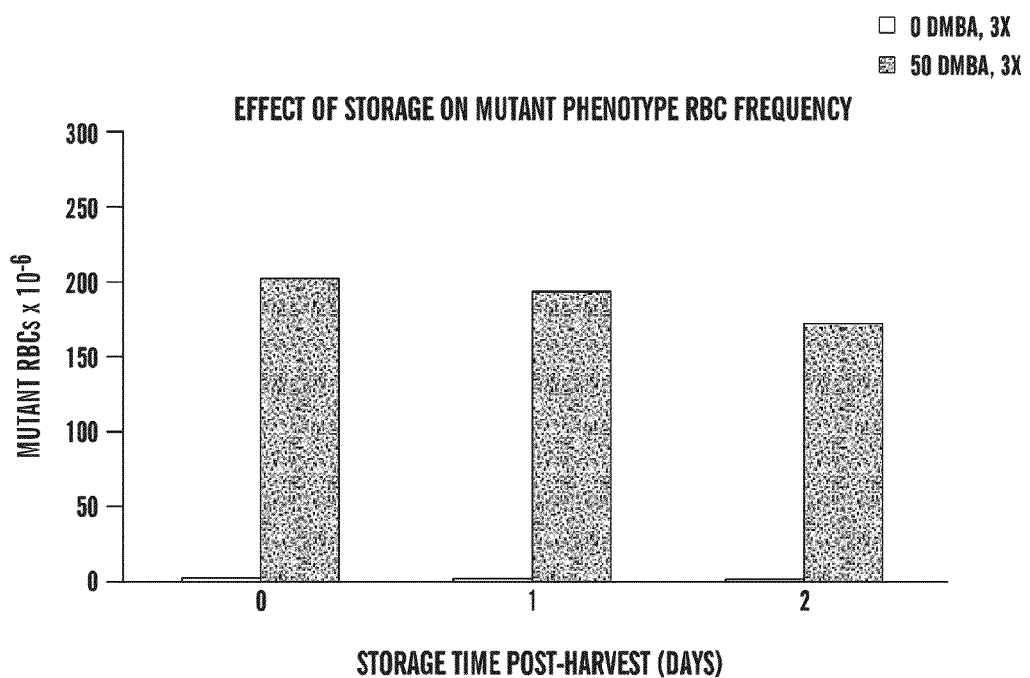
Figure 9C:
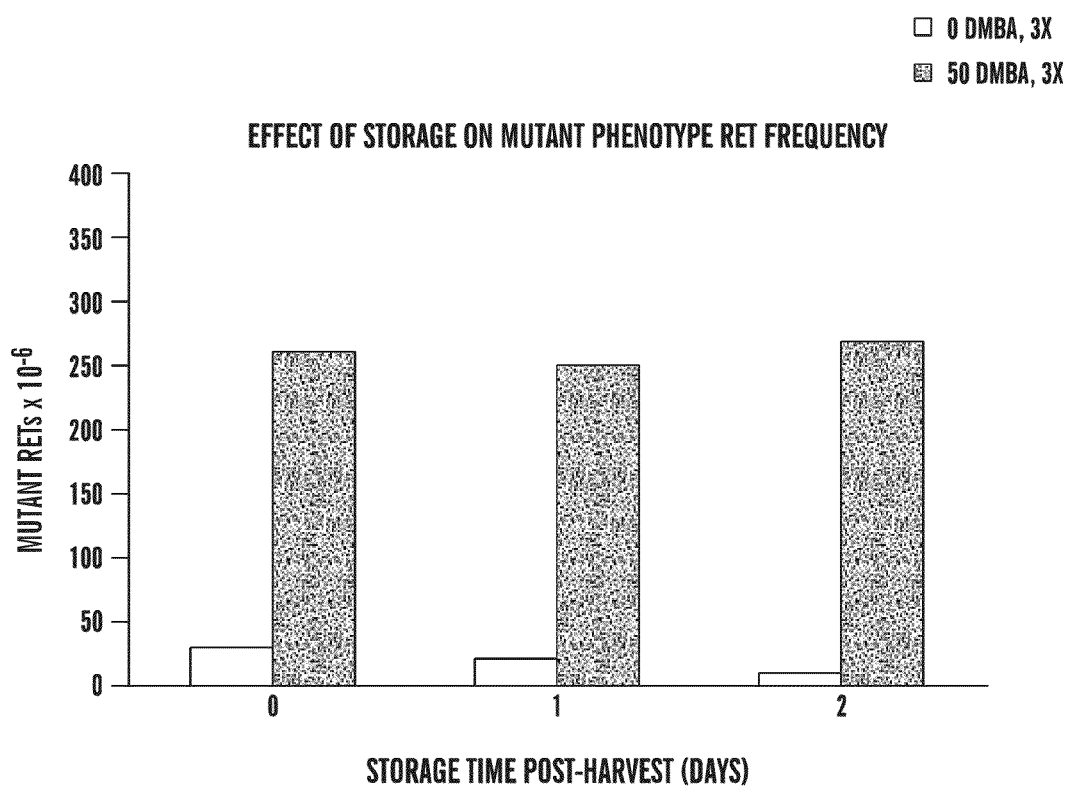

In this example, blood with a baseline mutation frequency (vehicle control rat) as well as an elevated mutation frequency (DMBA-treated rat) were collected. The specimens were each divided into three 30 μL aliquots that were processed through the leukodepletion step. After leukodepletion and washing with a balanced salt solution (PBS), one vehicle control fraction and one DMBA fraction were labeled with anti-CD59-PE and SYTO® 13 according to the present invention. The other two fractions that had been leukodepleted and washed were stored in a refrigerator for one or two days before being labeled with anti-CD59-PE and SYTO® 13 according to the present invention. The flow cytometry data are presented in FIGS. 9A-C. As shown in these figures, there were no substantial changes to the frequency of RETs, mutant phenotype RBCs, or mutant phenotype RETs over this period of time.

Collectively, the data presented herein demonstrate that flow cytometric scoring of GPI anchor-deficient RBCs and/or RETs represents an efficient means for measuring in vivo mutation frequency. This methodology affords a protocol for reliable assessment of chemical or physical agents for their ability to induce mutation, as well as a platform for determining which treatments are capable of diminishing or potentiating chemical or physical agent-induced mutation. As the Pig-A gene is highly conserved, this invention is expected to be applicable across mammalian species of toxicological interest, including man. For example, in humans the toxicity of new cancer therapies can be assessed for their degree of genotoxicity to non-target (i.e., non-cancerous) blood cells.

As compared to the previously described three-color method, the simpler two-color method of the present invention was found to be preferable in several respects: i) fewer fluorescent reagents reduces costs; ii) fewer fluorescent reagents reduces number of centrifugation steps required; iii) fewer fluorescent reagents simplifies flow cytometry instrument setup and calibration; iv) more stable nucleic acid dye allows one to batch process more samples at a time; v) simpler processing and flow cytometry instrument setup and calibration enhances transferability of the assay to other laboratories; and vi) following leukodepletion, enriched erythrocyte samples can be stored for at least 48 hours without adversely affecting the data, a feature that provides more latitude in terms of scheduling analyses and also facilitates shipment of samples to off-site analysis facilities. Regarding point v) above, based on a prototype kit containing instructions and reagents for practicing the present invention, one pharmaceutical company, in collaboration with the inventor, has already demonstrated that the assay is transferable to other laboratories. Regarding point vi) above, another researcher, also in collaboration with the inventor, has already demonstrated success in shipping leukodepleted blood samples for off-site performance of flow cytometric Pig-A analyses according to the present invention. In aggregate, all of these benefits will significantly reduce the time and labor costs associated with performing the assay, and improve the efficiency and reliability in obtaining the desired genotoxicity data.

All of the features described herein (including any accompanying claims, abstract and drawings), and/or all of the steps of any method or process so disclosed, may be combined with any of the above aspects in any combination, except combinations where at least some of such features and/or steps are mutually exclusive. Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of assessing mutagenic DNA-damaging potential of an agent comprising:
    subjecting a peripheral blood sample, obtained from a mammal exposed to an agent that may induce mutagenic DNA damage, to conditions effective to substantially separate erythrocytes from platelets and leukocytes, thereby forming an enriched erythrocyte sample;
    first contacting the enriched erythrocyte sample with a first reagent that binds GPI anchor-expressing erythrocytes, but not GPI anchor-deficient erythrocytes, wherein the first reagent comprises a first fluorochrome;
    second contacting the enriched erythrocyte sample with a second reagent that differentially labels normochromatic erythrocytes from reticulocytes and leukocytes, the second reagent comprising a second fluorochrome having a fluorescent emission spectrum that does not substantially overlap with the fluorescent emission spectra of the first fluorochrome;
    exciting the first and second fluorochromes with light having a wavelength suitable to induce fluorescence thereof; and
    detecting the fluorescent emission and light scatter produced by erythrocytes labeled with the first fluorochrome, while excluding nucleated cells but not reticulocytes labeled by the second fluorochrome, and counting the number of GPI anchor-deficient erythrocytes and/or reticulocytes relative to the number of total erythrocytes and/or reticulocytes, respectively, wherein a statistically significant deviation in the frequency of GPI-anchor-deficient erythrocytes and/or reticulocytes from a baseline frequency of GPI-anchor-deficient erythrocytes and/or reticulocytes in unexposed or vehicle control mammals indicates the mutagenic DNA-damaging potential of the agent.

2. The method according to claim 1 wherein the first reagent is anti-CD24, anti-CD59, and/or anti-CD55 antibody directly conjugated to the first fluorochrome, a non-lytic fluorescent aerolysin derivative, or a combination thereof.

3. The method according to claim 1 wherein the second fluorochrome-containing reagent is a nucleic acid dye.

4. The method according to claim 3, wherein the nucleic acid dye is a cyanine nucleic acid dye.

5. The method according to claim 1 wherein said first contacting and second contacting are carried out simultaneously.

6. The method according to claim 1 wherein said first contacting and second contacting are carried out sequentially.

7. The method according to claim 1 wherein said exciting is carried out with a single-laser or multiple-laser flow cytometer.

8. The method according to claim 1 wherein said detecting is carried out at a fluorescence threshold value set to eliminate mature erythrocytes that are not labeled with the second reagent, thereby restricting analysis to reticulocytes.

9. The method according to claim 1 further comprising:
    providing a second peripheral blood sample from the mammal prior to exposure to the agent;
    performing said subjecting, first contacting, second contacting, exciting, and detecting on the second sample; and
    comparing the results obtained from the first and second samples, wherein a statistically significant deviation in the frequency of GPI anchor-deficient erythrocytes and/or reticulocytes between the first and second samples indicates the mutagenic DNA damaging potential of the agent.

10. The method according to claim 1, wherein the agent is a chemical agent or a physical agent.

11. A method of evaluating the effects of an agent that may modify mutagenic DNA damage comprising:
    subjecting a peripheral blood sample obtained from a mammal exposed to an agent that may modify mutagenic DNA damage, to conditions effective to substantially separate erythrocytes from platelets and leukocytes, thereby forming an enriched erythrocyte sample;
    first contacting the enriched erythrocyte sample with a first reagent that binds GPI anchor-expressing erythrocytes, but not GPI anchor-deficient erythrocytes, wherein the first reagent comprises a first fluorochrome;
    second contacting the enriched erythrocyte sample with a second reagent that differentially labels normochromatic erythrocytes from reticulocytes and leukocytes, the second fluorescent reagent comprising a second fluorochrome having a fluorescent emission spectrum that does not substantially overlap with the fluorescent emission spectra of the first fluorochrome;

exciting the first and second fluorochromes with light having a wavelength suitable to induce fluorescence thereof; and detecting the fluorescent emission and light scatter produced by erythrocytes labeled with the first fluorochrome, while excluding nucleated cells but not reticulocytes labeled by the second fluorochrome, and counting the number of GPI anchor-deficient erythrocytes and/or reticulocytes relative to the number of total erythrocytes and/or reticulocytes, respectively, wherein a statistically significant deviation in the frequency of GPI anchor-deficient erythrocytes and/or reticulocytes from a baseline frequency of GPI anchor-deficient erythrocytes and/or reticulocyte indicates that the agent can modify mutagenic DNA damage.

12. The method of claim 11 further comprising:
exposing the mammal to a known mutagenic DNA damaging agent prior to said subjecting.

13. A method of assessing mutagenic DNA-damaging potential of an agent comprising:
contacting an enriched erythrocyte sample, which is substantially free of platelets and leukocytes and obtained from a mammal exposed to an agent that may induce mutagenic DNA damage, with (i) a first fluorescent reagent that binds GPI anchor-expressing erythrocytes but not GPI anchor-deficient erythrocytes, and (ii) a second fluorescent reagent that differentially labels normochromatic erythrocytes from reticulocytes and leukocytes, the second fluorescent reagent having a fluorescent emission spectrum that does not substantially overlap with a fluorescent emission spectrum of the first fluorescent reagent;

exciting the first and second fluorescent reagents with light having a wavelength suitable to induce fluorescence thereof; and detecting the fluorescent emission and light scatter produced by erythrocytes labeled with the first fluorescent reagent, while excluding nucleated cells but not reticulocytes labeled by the second fluorescent reagent, and counting the number of GPI anchor-deficient erythrocytes and/or reticulocytes relative to the number of total erythrocytes and/or reticulocytes, respectively, wherein a statistically significant deviation in the frequency of GPI-anchor-deficient erythrocytes and/or reticulocytes from a baseline frequency of GPI-anchor-deficient erythrocytes and/or reticulocyte in unexposed or vehicle control mammals indicates the DNA-damaging potential of the agent.

14. The method according to claim 13 wherein the first fluorescent reagent is anti-CD24, anti-CD59, and/or anti-CD55 antibody conjugated to a first fluorochrome, a non-lytic fluorescent aerolysin derivative, or a combination thereof.

15. The method according to claim 13 wherein the second reagent is a nucleic acid dye.

16. The method according to claim 15, wherein the nucleic acid dye is a cyanine nucleic acid dye.

17. The method according to claim 13 wherein said contacting with the first and second fluorescent reagents is carried out simultaneously.

18. The method according to claim 13 wherein said contacting with the first and second fluorescent reagents is carried out sequentially.

19. The method according to claim 13 wherein said exciting is carried out with a single-laser or multiple-laser flow cytometer.

20. The method according to claim 13 wherein said detecting is carried out at a fluorescence threshold value set to eliminate mature erythrocytes that are not labeled with the second fluorescent reagent, thereby restricting analysis to reticulocytes.

21. The method according to claim 13 further comprising:
performing said contacting, exciting, and detecting on a second enriched erythrocyte sample to obtain the baseline frequency, wherein the second enriched erythrocyte sample is substantially free of platelets and leukocytes and obtained from the mammal prior to exposure to the agent.

22. The method according to claim 13 wherein the agent is a chemical agent or physical agent.

* * * * *